US009886782B2

(12) United States Patent
Jo et al.

(10) Patent No.: US 9,886,782 B2
(45) Date of Patent: Feb. 6, 2018

(54) MEDICAL IMAGING APPARATUS AND MEDICAL IMAGE PROCESSING METHOD THEREOF

(71) Applicant: Samsung Electronics Co., Ltd., Gyeonggi-do (KR)

(72) Inventors: Hyun-hee Jo, Gyeonggi-do (KR); Praveen Gulaka, Gyeonggi-do (KR); Je-yong Shin, Gyeonggi-do (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 166 days.

(21) Appl. No.: 14/878,351

(22) Filed: Oct. 8, 2015

(65) Prior Publication Data
US 2016/0225140 A1 Aug. 4, 2016

(30) Foreign Application Priority Data
Jan. 29, 2015 (KR) .................. 10-2015-0014584

(51) Int. Cl.
*G06K 9/00* (2006.01)
*G06T 11/20* (2006.01)
(Continued)

(52) U.S. Cl.
CPC .......... *G06T 11/206* (2013.01); *A61B 5/0044* (2013.01); *A61B 5/055* (2013.01); *G06T 11/001* (2013.01); *G06T 2210/41* (2013.01)

(58) Field of Classification Search
USPC ........ 382/100, 103, 106–107, 128–133, 154, 382/162–168, 173, 181, 199, 219, 232,
(Continued)

(56) References Cited

U.S. PATENT DOCUMENTS 8,326,007 B2 12/2012 Langeland et al.
9,117,296 B2 * 8/2015 Stampanoni ........... A61B 6/483
(Continued)

FOREIGN PATENT DOCUMENTS

| JP | 2009-273882 A | 11/2009 |
|---|---|---|
| JP | 2012-105969 A | 6/2012 |
| JP | 2013-10005 A | 1/2013 |

OTHER PUBLICATIONS

Klein, et al.; "Reversibility Bull's Eye: A New Polar Bull's Eye Map to Quantify Reversibility of Stress-Induced SPECT Thallium-201 Myocardial Perfusion Defects"; The Journal of Nuclear Medicine; vol. 31; No. 7; Jul. 1, 1990.
(Continued)

*Primary Examiner* — Seyed Azarian
(74) *Attorney, Agent, or Firm* — Cha & Reiter, LLC.

(57) ABSTRACT

A medical imaging apparatus and a method of processing a medical image. The medical imaging apparatus includes: an image processor configured to respectively determine color values for subregions of an organ based on at least two of first through third analysis values for each of the subregions. A display outputs display of a first map image obtained by respectively mapping the determined color values to the subregions and indicating the determined color values on the subregions. In the case where the image of the organ is a heart, the different parts of the heart correspond to respective subregions, and an indication of a probability of disease corresponds to a plurality of colors in a color map of the regions.

24 Claims, 18 Drawing Sheets
(7 of 18 Drawing Sheet(s) Filed in Color)

(51) Int. Cl.
*G06T 11/00* (2006.01)
*A61B 5/00* (2006.01)
*A61B 5/055* (2006.01)
*A61B 5/05* (2006.01)

(58) Field of Classification Search
USPC ....... 382/254, 274, 276, 286–291, 305, 312; 378/4, 21; 600/407, 431, 410
See application file for complete search history.

(56) References Cited

U.S. PATENT DOCUMENTS

| | | |
|---|---|---|
| 2009/0295802 A1 | 12/2009 | Kushwaha et al. |
| 2010/0041992 A1 | 2/2010 | Ohuchi et al. |
| 2010/0246957 A1* | 9/2010 | Visser .................. G06T 19/003 382/173 |
| 2011/0007953 A1 | 1/2011 | Bernhardt et al. |
| 2011/0249005 A1 | 10/2011 | Hautvast |
| 2012/0263368 A1 | 10/2012 | Nakano et al. |
| 2012/0310074 A1* | 12/2012 | Yamamori ............. A61B 6/503 600/407 |
| 2012/0323118 A1* | 12/2012 | Menon Gopalakrishna ....... A61B 6/463 600/431 |
| 2013/0327713 A1 | 12/2013 | Jirka et al. |
| 2014/0169653 A1* | 6/2014 | Maack .................... G06T 11/60 382/132 |

OTHER PUBLICATIONS

Van Train, et al.; "Qualitative Analysis of Spect Myocardial Perfusion"; Cardiac Spect Imaging—Chapter 3; Jan. 1, 2001.
European Search Report dated Oct. 13, 2017.

* cited by examiner

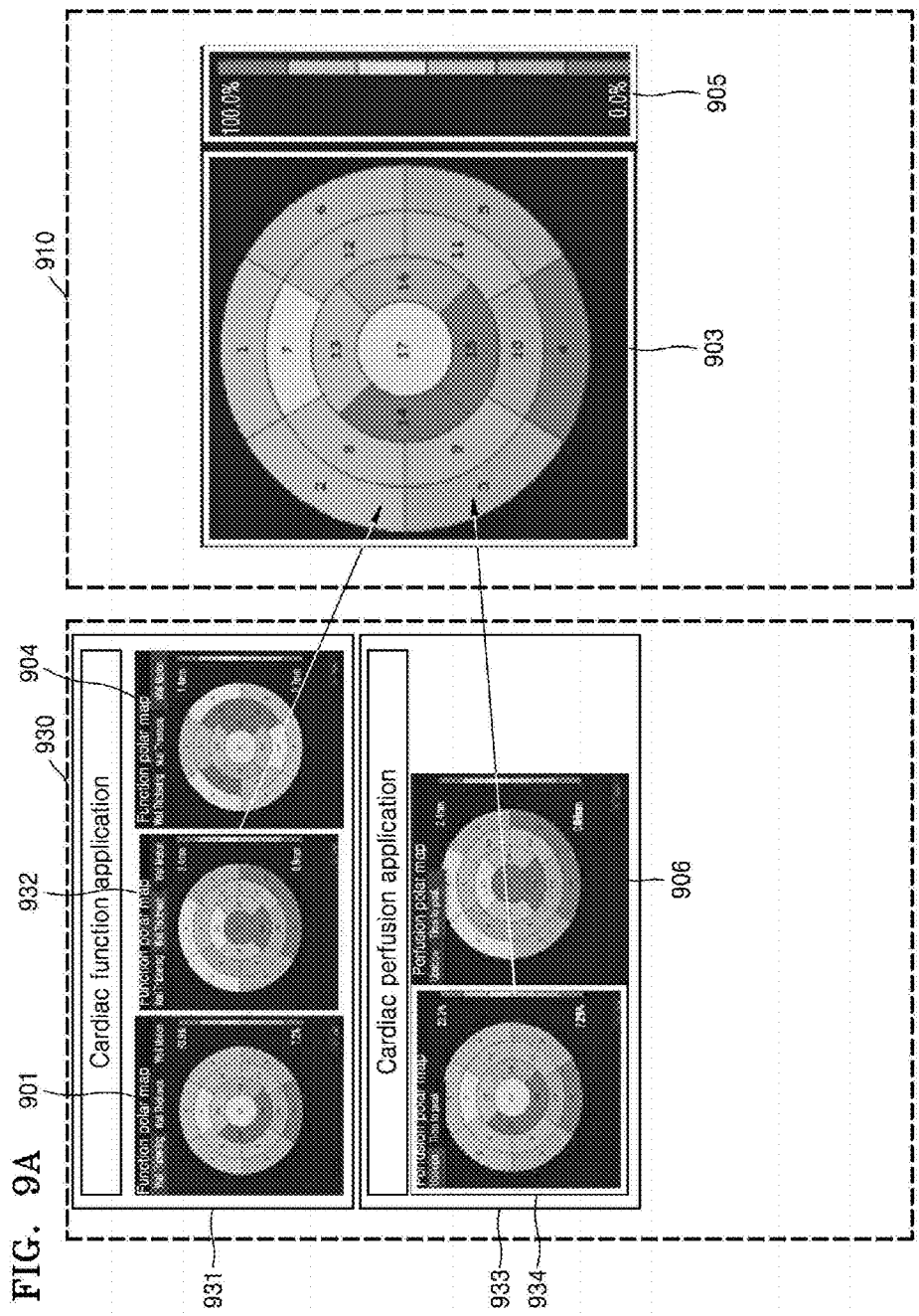

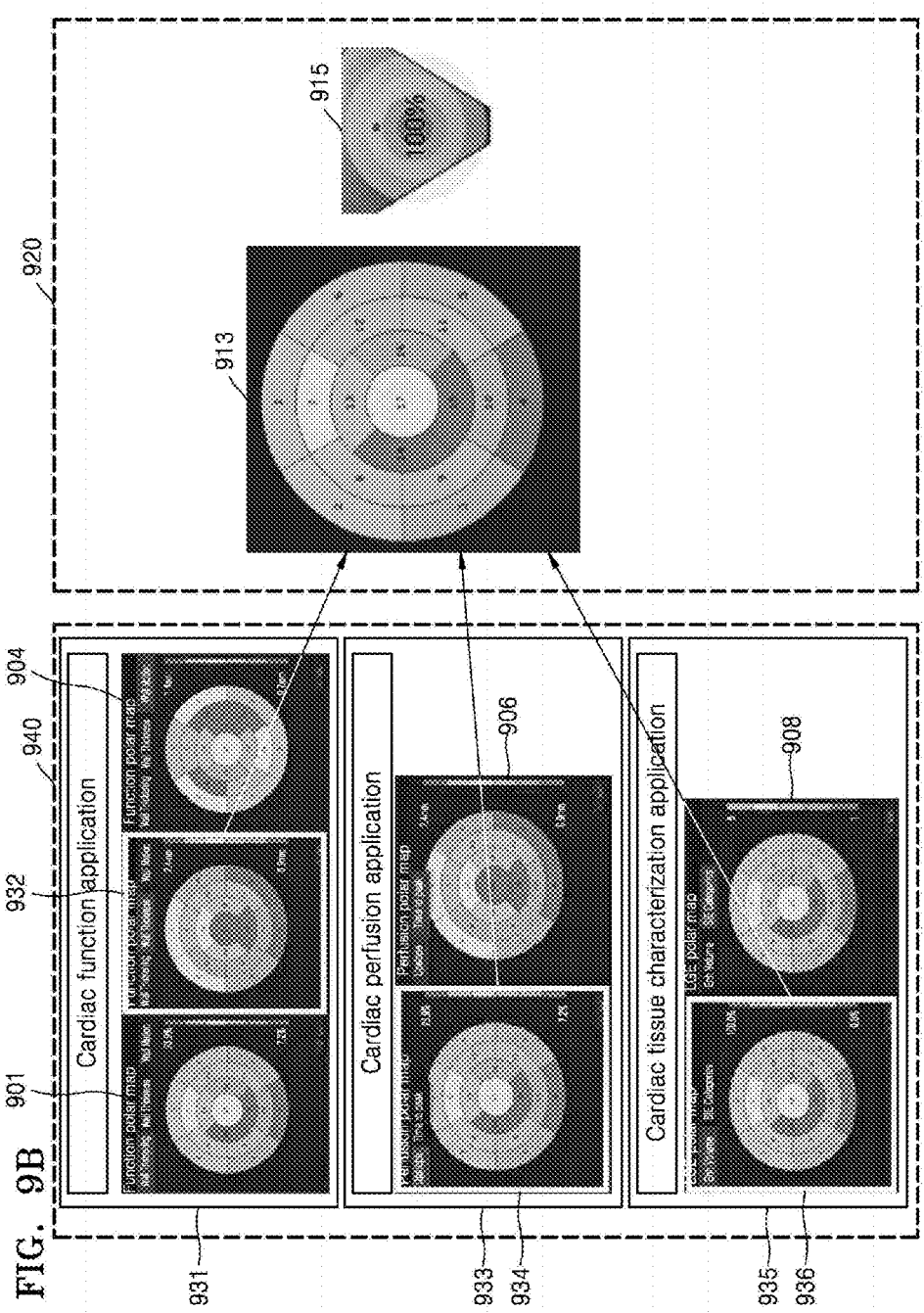

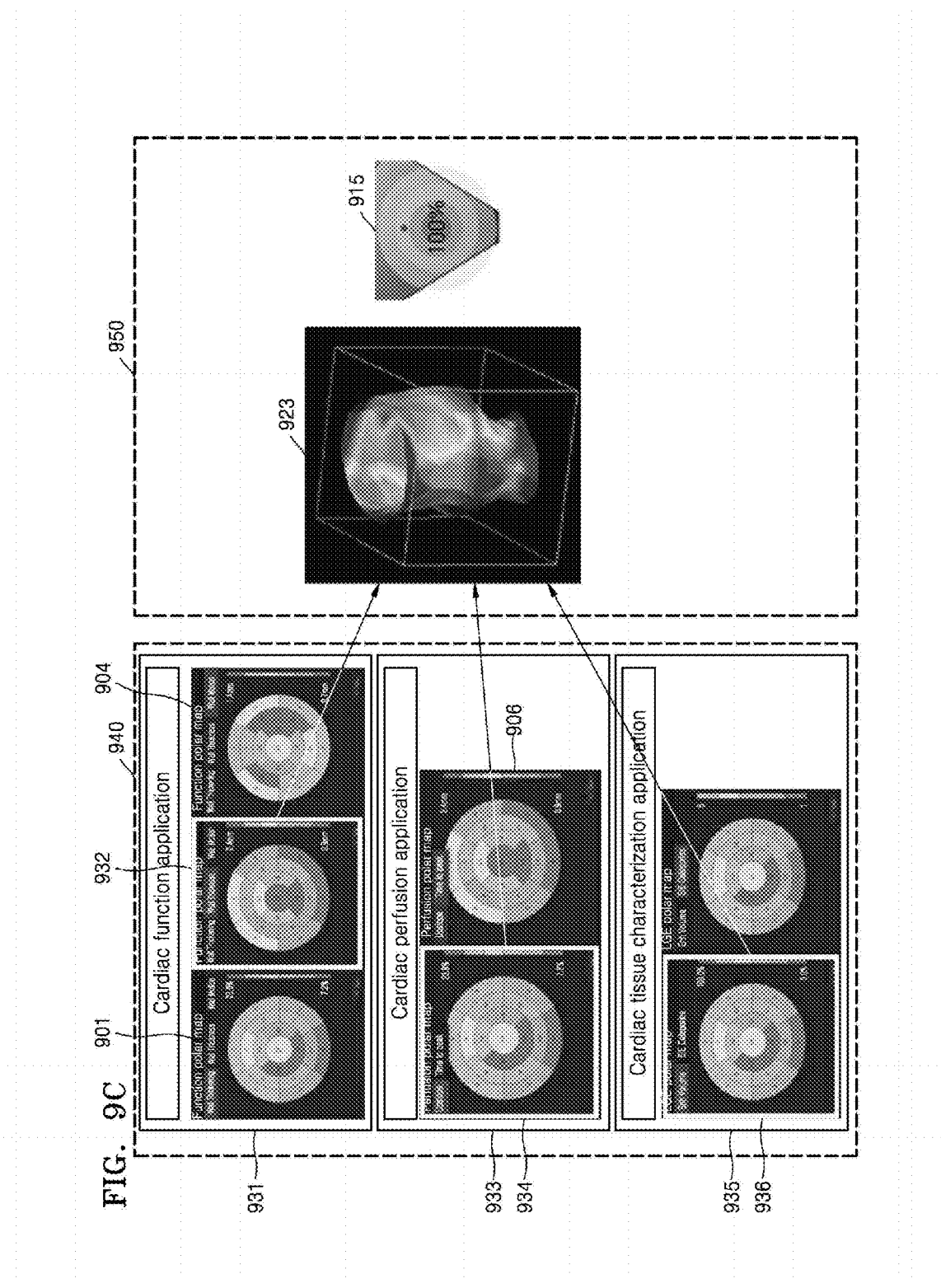

MEDICAL IMAGING APPARATUS AND MEDICAL IMAGE PROCESSING METHOD THEREOF

CLAIM OF PRIORITY

This application claims the benefit of priority from Korean Patent Application No. 10-2015-0014584, filed on Jan. 29, 2015, in the Korean Intellectual Property Office, the disclosure of which is incorporated by reference herein in its entirety.

BACKGROUND

1. Field of the Disclosure

The disclosure relates to an apparatus and method of processing a medical image. More particularly, the disclosure relates to an apparatus and method of processing a medical image capable of assessing the probability of disease in various parts of a heart.

2. Description of the Related Art

A medical imaging apparatus is an electronic device adapted to generate and process various types of medical images of a living object. The medical imaging apparatus is used typically to acquire an image showing the internal structure of the living object. Accordingly, the medical imaging apparatus captures and/or processes images of details of structures, tissues, flow of fluid, etc., inside a body and provides the images to a user. A user, e.g., a medical practitioner, may use images output from the medical image processing apparatus to diagnose a patient's condition and diseases. Various analytical applications have been developed to diagnose diseases that occur in various organs via the medical imaging apparatus. For example, the heart is a particularly complex organ that has various parts that are all subject to diseases that can be quite difficult to detect from an external examination.

SUMMARY

One or more exemplary embodiments of the disclosure are directed to a medical imaging apparatus and a medical image processing method that represents a combination of analysis values of parameters used for analysis of an object's condition and to diagnose disease, including but in no way limited to heart disease.

One or more exemplary embodiments of the disclosure include a medical imaging apparatus and a medical image processing method that allow a medical practitioner to intuitively determine a probability of developing heart disease in each of the various regions of the heart when the medical practitioner assesses the probability thereof based on colors indicated in a first map.

One or more exemplary embodiments of the disclosure include a medical imaging apparatus and a medical image processing method whereby the probability of heart disease may be assessed by combining three of a plurality of analysis values instead of a medical practitioner assessing the probability thereof based on each of the analysis values.

One or more exemplary embodiments include a medical imaging apparatus and a medical image processing method in which the accuracy of diagnosis may be further improved by applying a larger weight to an analysis value on which the user desires a diagnosis to be based, from among a plurality of analysis values.

Additional aspects will be set forth in part in the description which follows and, in part, will become apparent to a person of ordinary skill in the art from the description, or may be learned by practice of the presented exemplary embodiments.

According to one or more exemplary embodiments, a medical imaging apparatus includes: an image processor configured to respectively determine color values for subregions of an organ, such as a heart, based on at least two of a first through third analysis values for each of the subregions; and an output unit configured to display a first map image obtained by respectively mapping the determined color values to the subregions and indicating the determined color values on the subregions.

The first analysis value may be determined based on a function of a muscle for each of the subregions, and the second analysis value may be determined based on perfusion of the muscle for each of the subregions. The third analysis value may be determined based on characteristics of tissue of the muscle for each of the subregions.

The medical imaging apparatus may further include an input unit configured to receive a user input for selecting at least one of the first through third analysis values.

The image processor may map the first through third analysis values to first through third colors, respectively, and the color values may be determined by combining at least two of the first through third colors. The mapping can aid in diagnostic detection, and to determine a probability of disease.

The image processor may determine (i.e. designate) the color values by combining at least two of the first through third colors based on a weight for at least one of the first through third analysis values.

The output unit may display at least one of first through third additional images respectively indicating the first through third colors.

The output unit (i.e. display, for example), may further display at least one of a color bar image and a color map image which show probabilities of heart disease corresponding to a plurality of colors.

The display may output a graph related to at least one of the first through third analysis values.

The first map image may include at least one of a two-dimensional (2D) bull's eye map and a three-dimensional (3D) bull's eye map.

According to one or more exemplary embodiments, a method of processing a medical image includes: designating by an image processor color values for subregions of a heart, respectively, based on at least two of first through third analysis values for each of the subregions; and displaying a first map image obtained by respectively mapping the determined color values to the subregions and indicating the determined color values on the subregions.

The first analysis value may be determined based on a function of a muscle for each of the subregions, and the second analysis value may be determined based on perfusion of the muscle for each of the subregions. The third analysis value may be determined based on characteristics of tissue of the muscle for each of the subregions.

The method may further include receiving a user input for selecting at least one of the first through third analysis values.

The designating of the color values for the subregions of the heart may include mapping the first through third analysis values to first through third colors, respectively, and combining at least two of the first through third colors.

The designating of the color values by combining at least two of the first through third colors may include combining at least two of the first through third colors based on a weight for at least one of the first through third analysis values.

The displaying of the first map image may include further displaying at least one of first through third additional images respectively indicating the first through third colors.

The displaying of the first map image may further include displaying at least one of a color bar image and a color map image which show probabilities of heart disease corresponding to a plurality of colors.

The displaying of the first map image may include displaying a screen that further includes a third image including a graph related to at least one of the first through third analysis values.

The first map image may include at least one of a 2D bull's eye map and a 3D bull's eye map.

According to one or more exemplary embodiments, a non-transitory computer-readable recording medium has recorded thereon a program for executing the method of processing a medical image on a computer.

According to one or more exemplary embodiments, a medical imaging system includes the medical imaging apparatus and a signal transceiver configured to acquire a medical image.

According to one or more exemplary embodiments, it is possible to represent a combination of analysis values of parameters for diagnosing illness, such as heart disease.

Furthermore, according to one or more exemplary embodiments, the medical imaging apparatus and the medical image processing method allow the user to intuitively determine the probability of developing heart disease in each of the regions of a heart based on colors indicated in a first map.

Furthermore, according to one or more exemplary embodiments, the medical imaging apparatus and the medical image processing method allow the user to assess the probability of heart disease by combining at least two of a plurality of analysis values instead of assessing the probability thereof based on each of the analysis values. In this case, diagnosis by the user may be more accurate than when assessing the probability of heart disease based on only one of the analysis values.

Furthermore, according to one or more exemplary embodiments, accuracy of diagnosis may be further improved by applying a larger weight to an analysis value on which the user desires a diagnosis to be based, from among a plurality of analysis values.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

These and/or other aspects will become apparent and more readily appreciated by a person of ordinary skill in the art from the following description of the exemplary embodiments, taken in conjunction with the accompanying drawings in which:

FIG. 9A illustrates an example of a screen on which a first map image and a color bar image are displayed;

FIG. 9B illustrates an example of a screen on which a first map image and a color map image are displayed;

FIG. 9C illustrates another example of a screen on which a first map image and a color map image are displayed.

DETAILED DESCRIPTION

Figure 1:
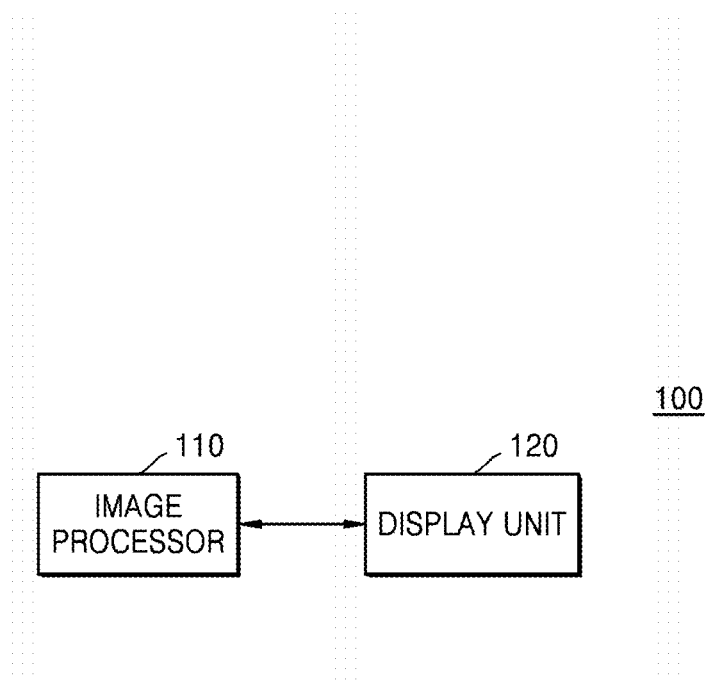
FIG. 1 is a block diagram of a magnetic resonance imaging (MRI) apparatus according to an embodiment of the disclosure.

Advantages and features of one or more embodiments of the present disclosure and methods of accomplishing the same may be understood more readily by reference to the following detailed description of the embodiments and the accompanying drawings. In this regard, the present embodiments may have different forms and should not be construed as being limited to the descriptions set forth herein. Rather, these embodiments are provided so that this disclosure will be thorough and complete and will fully convey the concept of the present embodiments to one of ordinary skill in the art, and the present disclosure will only be defined by the appended claims.

Terms used herein will now be briefly described and then one or more embodiments of the present disclosure will be described in detail.

All terms including descriptive or technical terms which are used herein should be construed as having meanings that are understood by one of ordinary skill in the art. However, the terms may have different meanings according to the intention of one of ordinary skill in the art, precedent cases, or the appearance of new technologies. Also, some terms may be arbitrarily selected by the applicant, and in this case, the meaning of the selected terms will be described in detail in the detailed description of the disclosure. Thus, the terms used herein have to be defined based on the meaning of the terms together with the description throughout the specification.

When a part "includes" or "comprises" an element, unless there is a particular description contrary thereto, the part can further include other elements, not excluding the other elements. Also, the term "unit" in the embodiments of the present disclosure refers to a software component executed by a hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components loaded into hardware for execution, as well as object-oriented software components, class components, and task components, that all may be loaded into hardware for execution, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

Reference will now be made in detail to embodiments, examples of which are illustrated in the accompanying drawings. In the following description, well-known functions or constructions are not described in detail so as not to obscure the embodiments with unnecessary detail.

In the present specification, an "image" may refer to multi-dimensional data composed of discrete image elements (e.g., pixels in a two-dimensional (2D) image and voxels in a three-dimensional (3D) image). For example, the image may be a medical image of an object captured by an X-ray apparatus, a computed tomography (CT) apparatus, a magnetic resonance imaging (MRI) apparatus, an ultrasound diagnosis apparatus, or another medical imaging apparatus.

Furthermore, in the present specification, an "object" may be a human, an animal, or a part of a human or animal. For example, the object may be an organ (e.g., the liver, the heart, the womb, the brain, a breast, or the abdomen), a blood vessel, or a combination thereof, just to name a few non-limiting illustrating examples. Furthermore, the "object" may be a "phantom". The phantom means a material having a density, an effective atomic number, and a volume that are approximately the same as those of an organism. For example, the phantom may be a spherical phantom having properties similar to the human body.

Furthermore, in the present specification, a "user" may be, but is not limited to, a medical practitioner, MRI technician, a medical expert, such as a medical doctor, a nurse, a medical laboratory technologist, or a technician who repairs a medical apparatus.

Furthermore, in the present specification, an "MR image" refers to an image of an object obtained by using the nuclear magnetic resonance principle.

Furthermore, in the present specification, a "pulse sequence" refers to continuity of signals repeatedly applied by an MRI apparatus. The pulse sequence may include a time parameter of a radio frequency (RF) pulse, for example, repetition time (TR) or echo time (TE).

Furthermore, in the present specification, a "pulse sequence schematic diagram" shows an order of events that occur in an MRI apparatus. For example, the pulse sequence schematic diagram may be a diagram showing an RF pulse, a gradient magnetic field, an MR signal, or the like according to time.

An MRI system in this disclosure refers to an apparatus for acquiring a sectional image of a part of an object by expressing, in a contrast comparison, a strength of a MR signal with respect to a radio frequency (RF) signal generated in a magnetic field having a specific strength. For example, if an RF signal that only resonates a specific atomic nucleus (for example, a hydrogen atomic nucleus) is emitted for an instant toward the object placed in a strong magnetic field and then such emission stops, an MR signal is emitted from the specific atomic nucleus, and thus the MRI system may receive the MR signal and acquire an MR image. The MR signal denotes an RF signal emitted from the object. An intensity of the MR signal may be determined according to a density of a predetermined atom (for example, hydrogen) of the object, a relaxation time $T1$, a relaxation time $T2$, and a flow of blood or the like.

MRI systems include characteristics different from those of other imaging apparatuses. Unlike imaging apparatuses such as CT apparatuses that acquire images according to a direction of detection hardware, MRI systems may acquire 2D images or 3D volume images that are oriented toward an optional point. MRI systems do not expose objects or examiners to radiation, unlike CT apparatuses, X-ray apparatuses, position emission tomography (PET) apparatuses, and single photon emission CT (SPECT) apparatuses, may acquire images having high soft tissue contrast, and may acquire neurological images, intravascular images, musculoskeletal images, and oncologic images that are required to precisely capturing abnormal tissues.

FIG. 1 is a block diagram of a medical imaging apparatus according to an embodiment of the disclosure.

The medical imaging apparatus may be, for example, a magnetic resonance imaging (MRI) apparatus, a tomography apparatus, an X-ray apparatus, or an ultrasound diagnosis apparatus, and may respectively process an MRI image, a tomography image, an X-ray image, or an ultrasound image.

It is assumed hereinafter that the medical imaging apparatus is an MRI apparatus 100 for processing an MRI image.

The MRI apparatus 100 of FIG. 1 may include an image processor 110 and an output unit 120.

The image processor 110, which comprises hardware such as a processor, microprocessor, controller, etc., may be configured to determine a color value for each of a plurality of subregions of a heart based on at least two of a plurality of analysis values for each subregion. In the present specification, the plurality of subregions of the heart are obtained by segmenting an area from a base to an apex of the heart. The base of the heart is a portion containing atria and large blood vessels, and the apex protrudes towards a lower part of the stomach. For example, the area from the base to the apex may be segmented into seventeen (17) subregions, as described in more detail below with reference to FIGS. 3 and 4. An artisan understands and appreciates that other organs in addition or in lieu of the heart can be imaged and assigned color values.

According to one or more disclosure embodiments, a plurality of analysis values may include, for example, first through third analysis values.

According to one or more disclosure embodiments of the disclosure, the first analysis value may be an analysis value related to a function of a cardiac muscle. The first analysis value may include an analysis value of a ventricular wall thickness, an analysis value for ventricular wall thickening, and an analysis value for a ventricular wall motion. For example, if a subregion has a low wall thickening value, the user may diagnose cardiomyopathy in the subregion.

The second analysis value may be an analysis value related to, for example, perfusion of a muscle, which is obtained by injecting a contrast medium into a cardiac muscle. The second analysis value may include a time-to-peak value and an upslope value representing a degree of contrast enhancement when a contrast medium is injected into muscle. The user/medical practitioner may diagnose the presence of heart disease and ischemic cardiac tissue based on the second analysis value. The ischemic cardiac tissue may be a tissue that does not receive enough blood flow due to blockage of a blood vessel. When a contrast medium is injected into a blood vessel within a cardiac muscle, the amount of contrast medium passing through the blood vessel may be expressed in a graphical representation. For example, if the user analyzes a graph of the amount of contrast medium for a subregion of the heart and finds that an upslope value in the graph is less than a normal value, this type of value indication that a blood vessel is not filled with a sufficient amount of blood during expansion of a ventricle. In this case, the user may diagnose cardiomyopathy in the subregion, or provide such information to a cardiologist to make or confirm such a diagnosis.

Furthermore, the third analysis value may be an analysis value for characteristics of cardiac muscle tissue. The third analysis value may include, for example, a late gadolinium enhancement (LGE) volume and an analysis value obtained via a Segmental Infarct Extent (SIE) category. In detail, the LGE volume and the analysis value obtained via the SIE category may be used to assess the extent of myocardial infarction among heart diseases. For example, if an LGE volume for a subregion is high, the user may diagnose necrosis of cardiac muscle tissue in the subregion.

Figure 4:
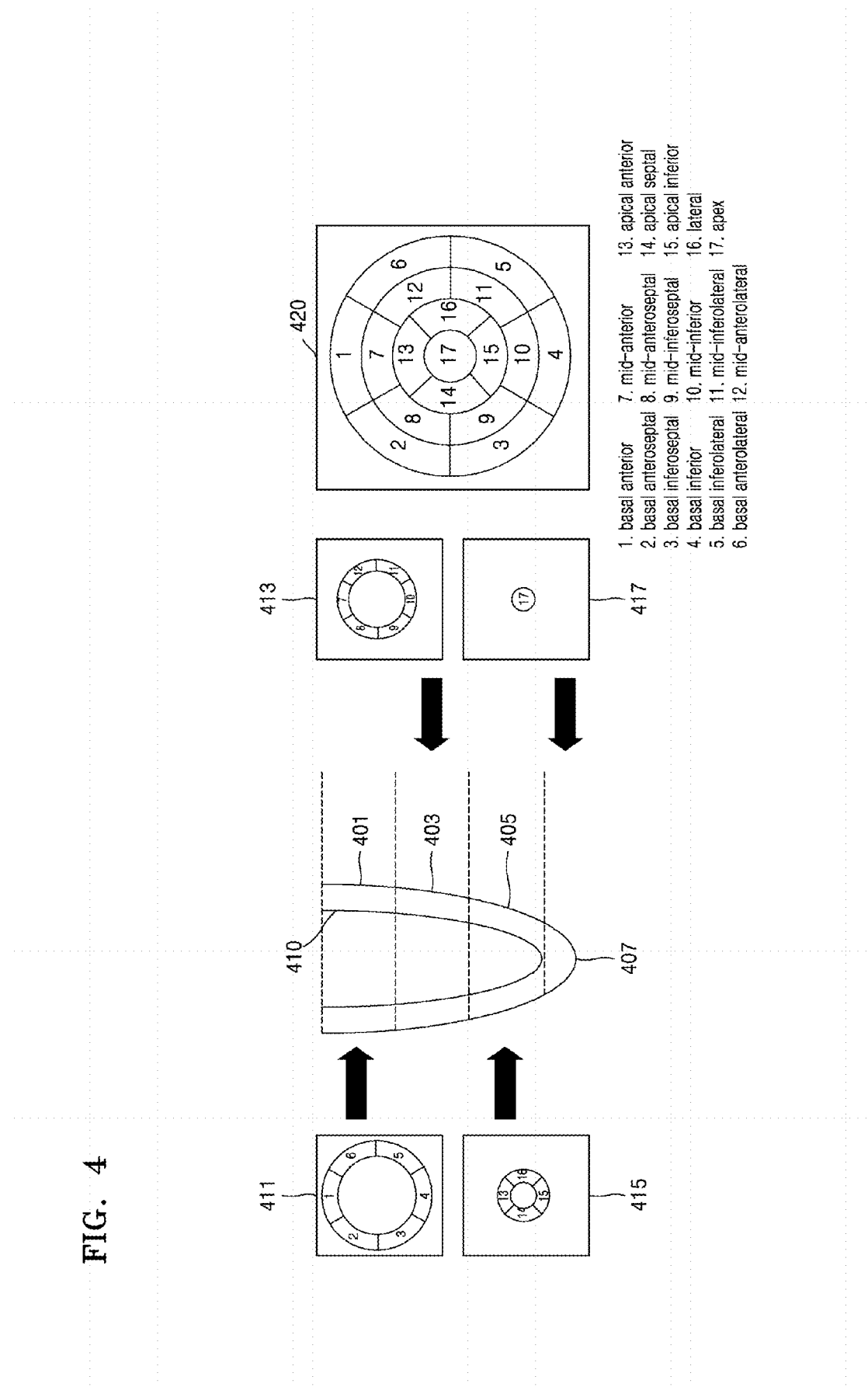
FIG. 4 illustrates a bull's eye map depicting subregions of the heart.

According to disclosure embodiments of the disclosure, the image processor 110 can be configured to determine color values for subregions indicated by numerals 1 through 17 in a polar map (polar map 420 of FIG. 4). The subregions 1 through 17 may respectively correspond to a plurality of subregions of the heart. In detail, the image processor 110 may determine a color value for each of the plurality of subregions based on at least two of first through third analysis values for each of the subregions 1 through 17. A method of determining color values for the subregions will also be described in more detail below with reference to FIGS. 8 through 10.

According to a disclosure embodiment, the output unit 120 comprises a display that outputs an image of a first map image obtained by respectively mapping determined color values to a plurality of subregions of the heart and indicating the determined color values thereon.

In the present specification, a 'first map image' may be an image displayed by respectively mapping color values for a plurality of subregions to subregions of the heart. For example, the first map image may include a bull's eye map. The bull's eye map may be an image displayed by respectively mapping color values, which are determined based on at least two analysis values, to the subregions of the heart. For example, the bull's eye map may be a two-dimensional (2D) bull's eye map displaying color values in the subregions 1 through 17 in the polar map 420 or a three-dimensional (3D) bull's eye map displaying color values in 3D subregions. However, an artisan appreciates and understands that within the scope of the claims there can be other types of maps.

For convenience, an image indicating color values determined based on a plurality of analysis values is hereinafter referred to as a 'first map image', and an image indicating color values determined based on one analysis value is referred to as a 'bull's eye map'.

Figure 2:
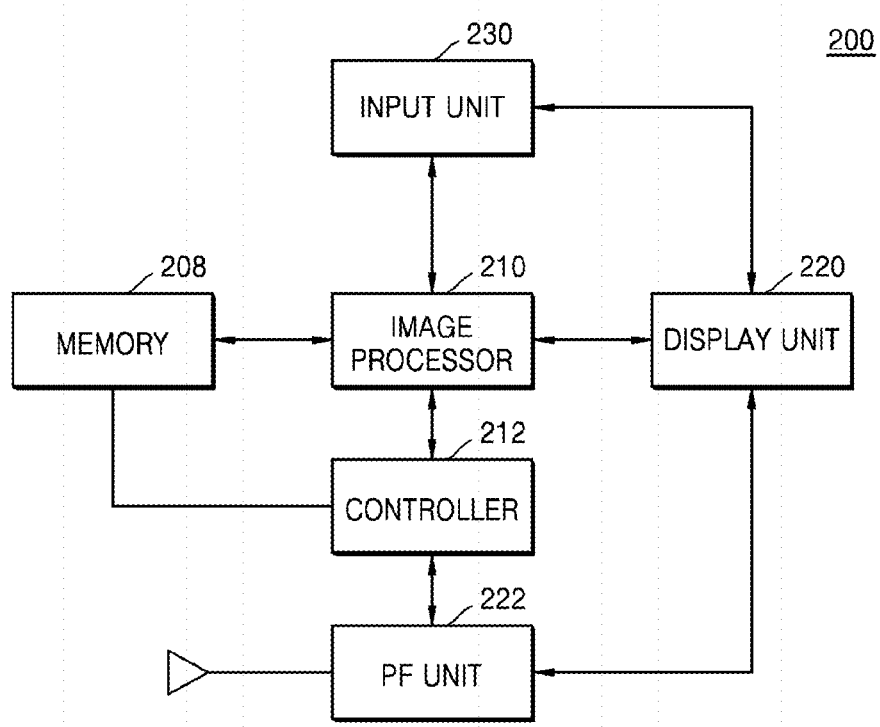
FIG. 2 is a block diagram of an MRI apparatus according to another embodiment of the disclosure.

FIG. 2 is a block diagram of an MRI apparatus 200 according to another disclosure embodiment.

Referring now to FIG. 2, the MRI apparatus 200 according to the present disclosure embodiment may include a non-transitory memory 208 for storing images, an image processor 210, a controller 212, an output unit 220, RF unit 222 and an input unit 230.

The image processor 210 and the output unit (i.e. display) 220 shown in FIG. 2 may correspond to the image processor 110 and the output unit (display) 120 shown in FIG. 1, respectively. Descriptions that are already provided above with respect to FIG. 1 will be omitted here. Non-transitory memory 208 can store previously-obtained images, or a current image. Controller 212 comprises hardware such as a microprocessor configured for operation and may be part of or separate from the image processor 210. RF unit can acquire or transmit an image of an object, and an acquired image may be sent to/from the MRI apparatus.

The MRI apparatus 200 may include a user input unit 230 that may be a virtual keypad, notebook, etc. The input unit 230 may be a unit via which the user inputs data necessary for controlling the MRI apparatus 200.

According to one or more disclosure embodiments of the present disclosure, the input unit 230 may receive a user input for selecting at least one of first through third analysis values that are related to the organ being imaged, For example, in the case of the organ being a heart, Different types of the first analysis value related to a function of a cardiac muscle may include an analysis value of a ventricular wall thickness, an analysis value for ventricular wall thickening, and an analysis value for a ventricular wall motion. Different types of the second analysis value related to perfusion of a muscle may include a time-to-peak value and an upslope value representing a degree of contrast enhancement when a contrast medium is injected into a muscle. Different types of the third analysis value related to characteristics of cardiac muscle tissue may include an LGE volume and an analysis value obtained via an SIE category. Furthermore, the user may select an analysis value for ventricular wall thickening as the first analysis value, an upslope value as the second analysis value, and an LGE volume as the third analysis value. The user may select for display all, or one, or a plurality of the first through third analysis values. At least one of the first through third analysis values may be preset.

Furthermore, the input unit 230 may receive an input for selecting at least two of the first through third analysis values related to color values to be displayed via a first map image.

For example, if the user desires to display only a color value determined based on the first and second analysis values via the first map image, the user may select the first and second analysis values.

As another example, if the user desires to display a color value determined based on the first through third analysis values via the first map image, the user may select the first through third analysis values.

The input unit 230 may also receive a user input for selecting a weight for at least one of the first through third analysis values. For example, if the user makes a diagnosis that focuses on whether cardiac muscle tissues include ischemic tissue, the user may select 0.1, 0.8, and 0.1 as weights for the first through third analysis values, respectively, via the user input unit 230. Furthermore, the input unit 230 may receive a user input for selecting a subregion in a first map image displayed by the output unit 220. The output unit 230 may display a value for at least one of the first through third analysis values for the subregion selected based on the user input. According to another embodiment, the output unit 220 may display a graph related to at least one of the first through third analysis values.

In the specification, it has been described that analysis values related to color values to be displayed via a first map image include first through third analysis values. However, the embodiments are not limited thereto, and the analysis values may further include other analysis values.

Figure 3:
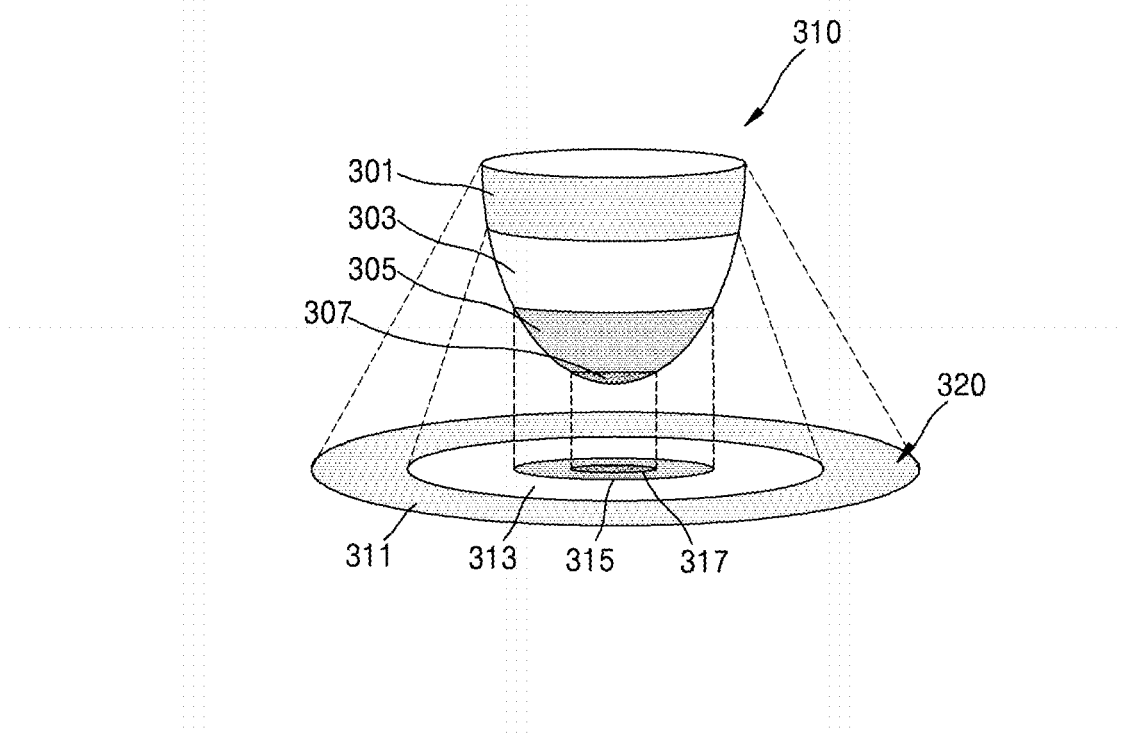
FIG. 3 is a diagram of the heart 310 with regions in different colors according to an embodiment of the disclosure.

FIG. 3 is a diagram of the heart 310 for explaining regions of the heart 310 according to an embodiment.

Referring now to FIG. 3, the heart 310 is divided into a base portion 301, a mid portion 303, an apex portion 305, and an apex 307. The base portion 301, the mid portion 303, the apex portion 305, and the apex 307 of the heart may be mapped onto a planar area 320. The planar area 320 may include first through fourth regions 311, 313, 315, and 317. The first through fourth regions 311, 313, 315, and 317 may correspond to the base portion 301, the mid portion 303, the apex portion 305, and the apex 307, respectively.

FIG. 4 illustrates a bull's eye map depicting subregions of the heart.

FIG. 4 shows a longitudinal section 410 of the heart 310 of FIG. 3. The longitudinal section 410 may be perpendicular to the planar area 320. A base sub-section 401, a mid portion sub-section 403, an apex sub-section 405, and an apex 407 included in the longitudinal section 410 may correspond to the base portion 301, the mid portion 303, the apex portion 305, and the apex 307, respectively. Furthermore, if the base sub-section 401, the mid portion sub-section 403, the apex sub-section 405, and the apex 407 are mapped onto a planar area, the base sub-section 401, the mid portion sub-section 403, the apex sub-section 405, and the apex 407 may correspond to first through fourth regions 411, 413, 415, and 417, respectively. Each of the first through fourth regions 411, 413, 415, and 417 may be partitioned into a plurality of subregions.

The first region 411 corresponding to the base sub-section 401 may be divided into subregions 1 through 6. The second region 413 corresponding to the middle portion sub-section 403 may be divided into subregions 7 through 12. The third region 415 corresponding to the apex sub-section 405 may be divided into subregions 13 through 16. In addition, a subregion indicated by numeral 17 may represent the apex 407.

The subregions 1 through 17 in the polar map 420 shown in FIG. 4 include the subregions 1 through 6 of the first region 411, the subregions 7 through 12 of the second region 413, the subregions 13 through 16 of the third region 415, and the subregion 17 of the fourth region 417.

Below the polar map 420, portions of the heart 310 respectively corresponding to the subregions 1 through 17 are illustrated.

An analysis value representing characteristics of each of the subregions 1 through 17 in the polar map 420 may be indicated on the subregion. In this way, an image representing a color on each of the subregions 1 through 17 in the polar map 420 may be referred to as a bull's eye map. An analysis value for each of the sub-regions 1 through 17 may include a first analysis value related to a function of a cardiac muscle, a second analysis value related to perfusion of a muscle, and a third analysis value related to characteristics of a muscle tissue.

Figure 5:
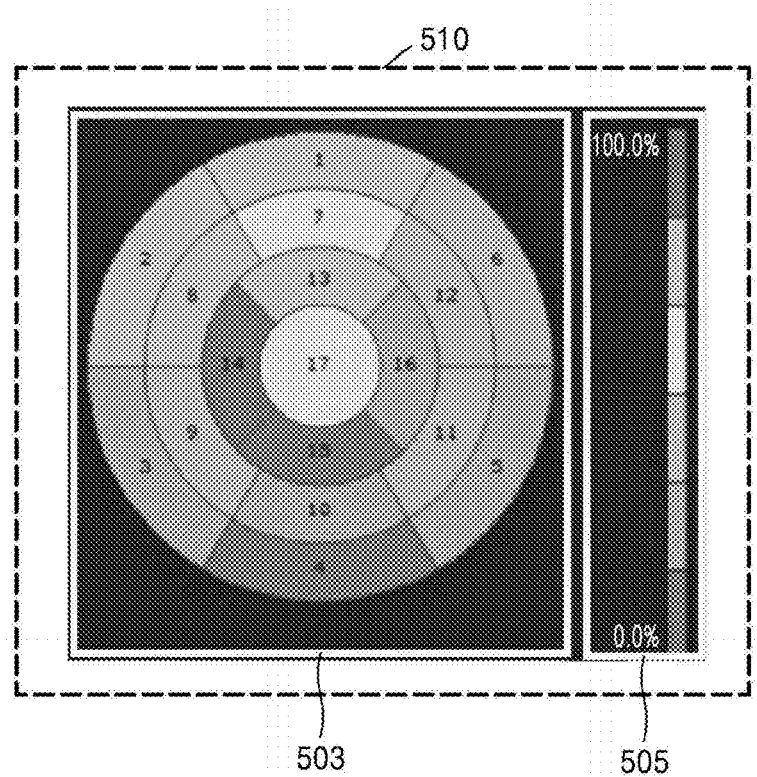
FIG. 5 is a color drawing that illustrates a bull's eye map according to an embodiment of the disclosure.

FIG. 5 illustrates a 2D bull's eye map 503 according to an embodiment. Referring to FIG. 5, the 2D bull's eye map 503 depicting color values on subregions indicated by numerals 1 through 17 is illustrated. The 2D bull's eye map 503 may be displayed together with a color bar image 505 representing probabilities of heart disease corresponding to a plurality of colors. In detail, the probabilities of heart disease corresponding to colors represented in the subregions 1 through 17 may be shown in the color bar image 505. For example, the probabilities of heart disease corresponding to green and red colors represented in the subregions 14 and 15 may be approximately close to 100% and 0%, respectively.

The user may intuitively diagnose the presence of disease in a certain portion of the heart based on a color value indicated on the 2D bull's eye map 503 displayed on the output unit 120 of the MRI apparatus 100. For example, the user may determine that the probability of the presence of heart disease near an apical septal region is 80% through 100%.

Figure 6:
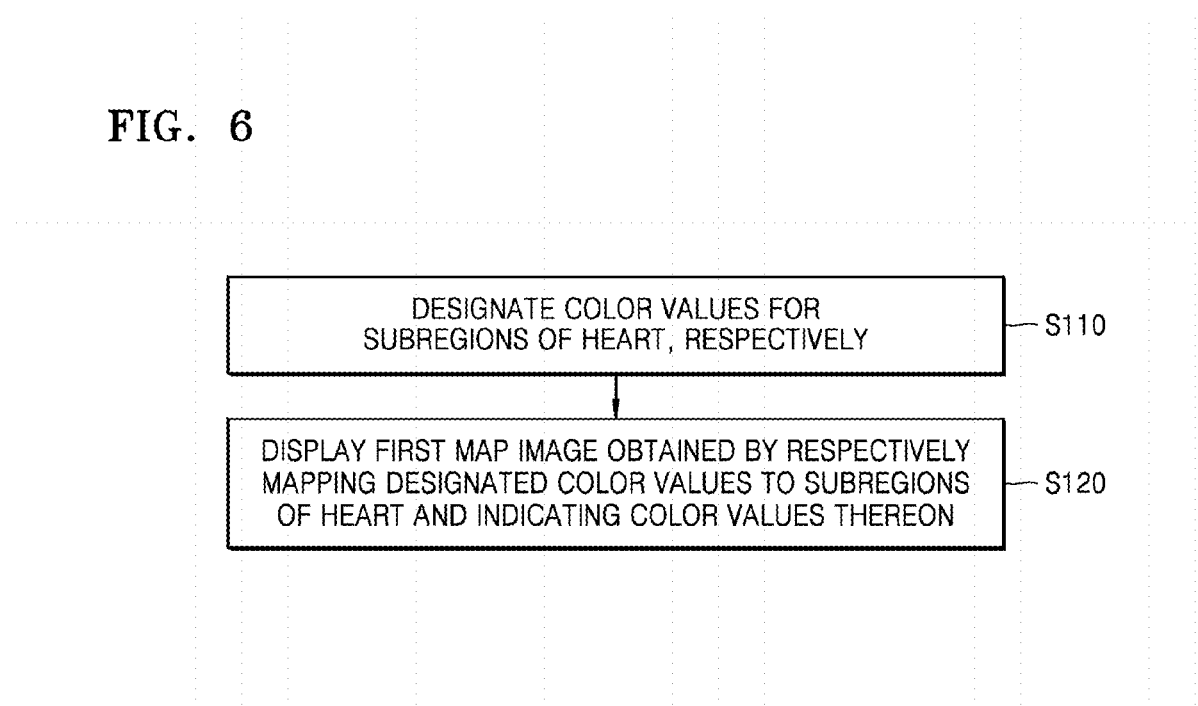
FIG. 6 is a flowchart of a medical image processing method performed by the MRI apparatus of FIG. 1, according to an embodiment of the disclosure.

FIG. 6 is a flowchart of a medical image processing method performed by the MRI apparatus of FIG. 1, according to an embodiment of the disclosure.

The MRI apparatus 100 may respectively determine color values for subregions of the heart, based on at least two of first through third analysis values for each of the subregions (S110).

In this case, the first analysis value may be determined based on a function of a muscle for each of the subregions. The second analysis value may be determined based on perfusion of a muscle for each of the subregions. The third analysis value may be determined based on characteristics of a muscle tissue for each of the subregions.

The MRI apparatus 100 may display a first map image obtained by respectively mapping the determined color values to the subregions of the heart and indicating the determined color values thereon (S120). The first map image may be displayed by mapping a color value determined in operation S110 to each of the subregions.

Figure 7:
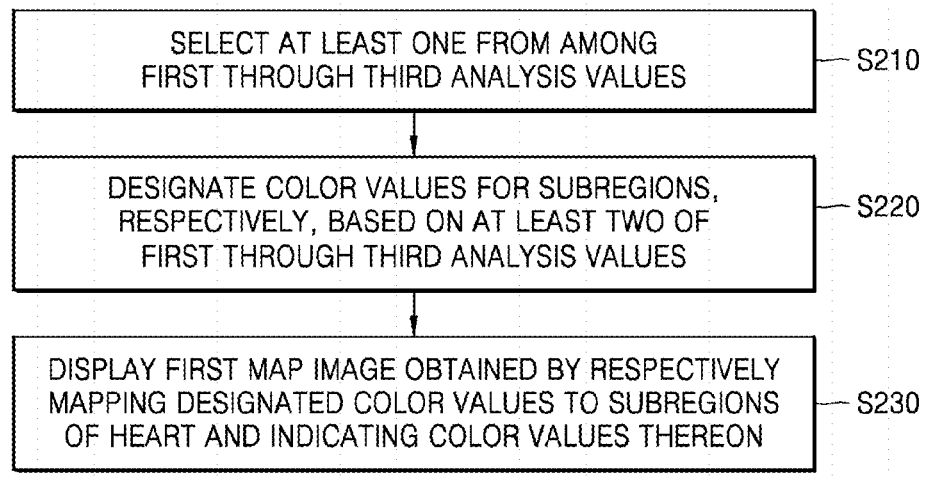
FIG. 7 is a flowchart illustrating operation of a medical image processing method performed by the MRI apparatus of FIG. 2, according to an embodiment of the disclosure.

FIG. 7 is a flowchart of a medical image processing method performed by the MRI apparatus of FIG. 2, according to an embodiment of the disclosure.

The MRI apparatus 200 may receive a user input for selecting at least one from among first through third analysis values (S210). As described above, for example, the user may select an analysis value for ventricular wall thickening as a type of the first analysis value, an upslope value as a type of the second analysis value, and an LGE volume as a type of the third analysis value.

The MRI apparatus 200 may respectively determine color values for subregions based on at least two of the first through third analysis values (S220).

The MRI apparatus 200 may display a first map image obtained by respectively mapping the determined color values to the subregions and bull's eye map the determined color values thereon (S230). Since operations S220 and S230 correspond to operations S110 and S120 shown in FIG. 6, respectively, detailed descriptions thereof will be omitted here.

Figure 8:
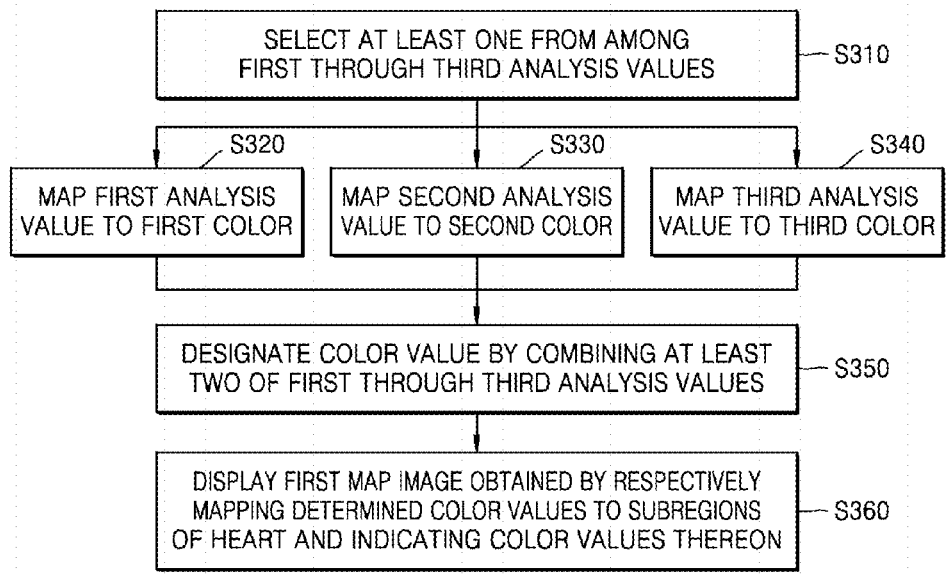
FIG. 8 is a flowchart illustrating operation of a medical image processing method performed by the MRI apparatus of FIG. 2, according to another embodiment of the disclosure.

FIG. 8 is a flowchart of a medical image processing method performed by the MRI apparatus of FIG. 2, according to another embodiment of the disclosure.

Referring now to FIG. 8, the MRI apparatus 200 may receive a user input for selecting at least one from among first through third analysis values (S310). For example, the user may select an analysis value for ventricular wall thickening as a type of the first analysis value, an upslope value as a type of the second analysis value, and an LGE volume as a type of the third analysis value.

The MRI apparatus 200 may map the first analysis value to a first color (S320).

Figure 10A:
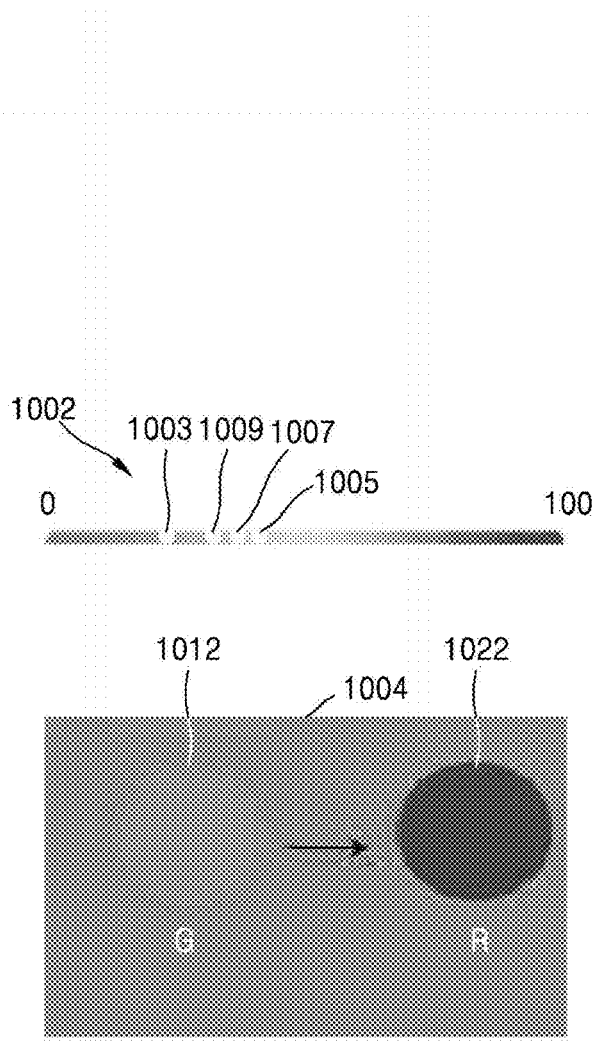
FIG. 10A, FIG. 10B and FIG. 10C are color diagrams for illustrating different aspects of a method of determining a color value by combining at least two colors.
Figure 10B:
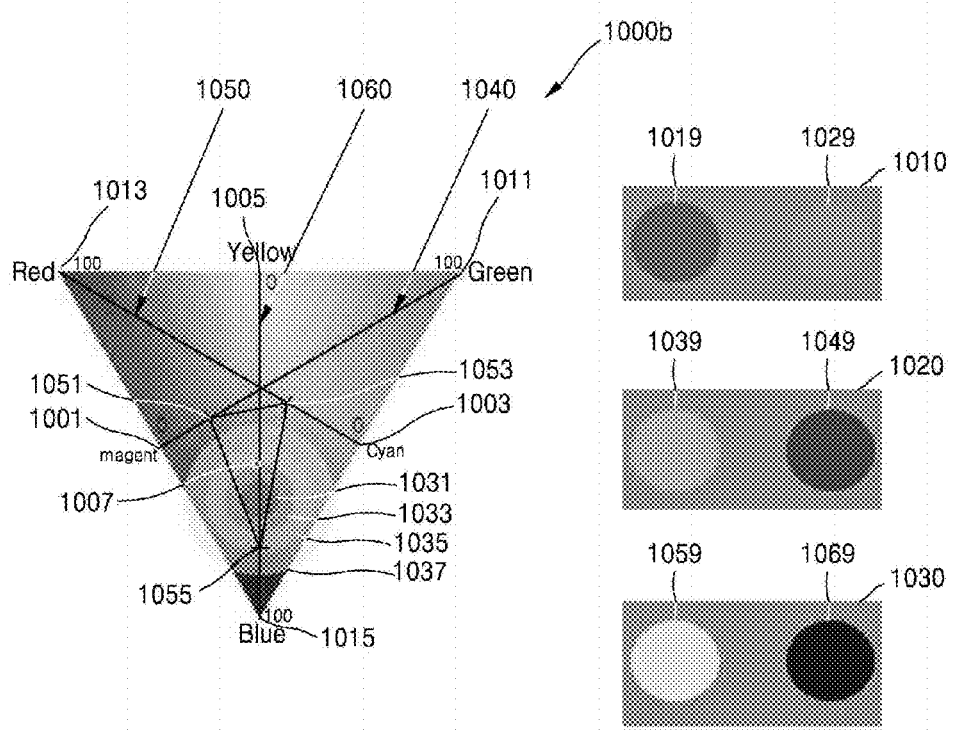

For example, referring now to FIG. 10B, the first analysis value may be mapped to coordinates 1051 on a first color coordinate axis 1040 corresponding to the first analysis value. Furthermore, the coordinates 1051 on the first color coordinate axis 1040 may be mapped to a first color corresponding to the coordinates 1051. As shown in FIG. 10B, the first color may be a color at a location indicated by the coordinates 1051.

The MRI apparatus 200 may map the second analysis value to a second color (S330).

For example, referring to FIG. 10B, the second analysis value may be mapped to coordinates 1053 on a second color coordinate axis 1050 corresponding to the second analysis value. Furthermore, the coordinates 1053 on the second color coordinate axis 1050 may be mapped to a second color corresponding to the coordinates 1053. As shown in FIG. 10B, the second color may be a color at a location indicated by the coordinates 1053.

Similarly, the MRI apparatus 200 may map the third analysis value to a third color (S340).

For example, referring to FIG. 10B, the third analysis value may be mapped to coordinates 1055 on a third color coordinate axis 1060 corresponding to the third analysis value. Furthermore, the coordinates 1055 on the third color coordinate axis 1060 may be mapped to a third color corresponding to the coordinates 1055. As shown in FIG. 10B, the third color may be a color at a location indicated by the coordinates 1055.

The MRI apparatus 200 may determine (designate) a color value by combining at least two of the first through third analysis values (S350).

For example, referring to FIG. 10B, the MRI apparatus 200 may determine a color value by combining at least two of the first through third colors respectively corresponding to the coordinates 1051, 1053, and 1055. According to one or more embodiments, the determined color value may be a value of coordinates 1007 of a barycenter in a triangle formed by three points respectively having the coordinates 1051, 1053, and 1055. As another example, the MRI apparatus 200 may determine a color value by combining at least two of the first through third colors, based on a weight for at least two of the first through third analysis values.

The MRI apparatus 200 may display a first map image obtained by respectively mapping determined color values to subregions of the heart (S360).

For example, the MRI apparatus 200 may display a first map image representing on a subregion a color of a portion where coordinates 1007 corresponding to a determined color value as shown in FIG. 10B are indicated.

FIGS. 9A through 9C are color diagrams for illustrating a first map image 903 according to an embodiment of the disclosure.

FIG. 9A illustrates an example of a screen 910 on which the first map image 903 and a color bar image 905 are displayed.

The first map image 903 may be created based on a first analysis value obtained via a cardiac function application 931 and a second analysis value obtained via a cardiac perfusion application 933. A screen 930 where the cardiac function application 931 and the cardiac perfusion application 933 are executed is illustrated for convenience of explanation and may not be displayed on the output unit 120 (220) according to the embodiments.

The color bar image 905 may indicate the probability of heart disease corresponding to a color indicated on the first map image 903.

According to the present embodiment, types of the first analysis value may include an analysis value of a ventricular wall thickness, an analysis value for ventricular wall thickening, and an analysis value for a ventricular wall motion. The MRI apparatus 100 (200) may generate, for example, bull's eye map images 901, 932, and 904 based on the first analysis value via the cardiac function application 931. Furthermore, the MRI apparatus 100 (200) may display at least one of the bull's eye map images 901, 932, and 904 respectively generated based on the analysis value for ventricular wall thickening, the analysis value of a ventricular wall thickness, and the analysis value for a ventricular wall motion, together with the first map image 903. According to the example shown in FIG. 9A, a user may select the analysis value of the ventricular wall thickness from among types of the first analysis value in order to generate the first map image 903.

The second analysis value may include a time-to-peak value and an upslope value representing the degree of contrast enhancement when a contrast medium is injected into a muscle. The MRI apparatus 100 (200) may generate bull's eye map images 934 and 906 based on the second analysis value via the cardiac function application 931. Furthermore, the MRI apparatus 100 (200) may display at least one of the bull's eye map images 934 and 906 respectively generated based on the upslope value and the time-to-peak value, together with the first map image 903. According to the example shown in FIG. 9A, the user may select the upslope value from among types of the second analysis value in order to generate the first map image 903.

A color value of a subregion in the first map image 903 may be determined based on the first and second analysis values. For example, the MRI apparatus 100 (200) may determine a color value for the first map image 903 by combining first and second colors respectively represented on the bull's eye map images 932 and 934. In detail, the MRI apparatus 100 (200) may determine a value of a color represented in subregion 1 of the first map image 903 by combining colors respectively represented in subregion 1 of the bull's eye map image 932 and subregion 1 of the bull's eye map image 934. Similarly, values of colors represented in subregions 2 through 17 of the first map image 903 may be determined in the same manner as described above.

Furthermore, the user may assign different weights to the first and second analysis values. For example, the user may assign weights of 0.1 and 0.9 to the first and second analysis values, respectively. A method of combining the first and second colors respectively corresponding to the first and second analysis values will be described in more detail later with reference to FIGS. 10A, 10B and 10C herein below.

According to the embodiment shown in FIG. 9A, if the user assesses the probability of heart disease based on a color indicated in a first map, it is possible to intuitively determine the probability of heart disease for each subregion of the heart.

Furthermore, the user may assess the probability of heart disease based on a combination of both the first and second analysis values instead of using the first and second analysis values individually. According to this method, the user may make a more accurate diagnosis than when assessing the probability of heart disease based on only one of the first and second analysis values.

Furthermore, the user may further improve accuracy of diagnosis by applying a larger weight to one of the first and second analysis values, on which the user desires to base the diagnosis.

FIG. 9B illustrates an example of a screen 940 on which a first map image 913 and a color map image 915 are displayed.

The color map image 915 shows the probability of heart disease corresponding to a color in the color map image 915.

The probability of heart disease corresponding to a color shown in a circle of a central portion of the color map image 915 may be 100%.

The first map image 913 may be created based on at least two of a first analysis value obtained via a cardiac function application 931, a second analysis value obtained via a cardiac perfusion application 933, and a third analysis value obtained via a cardiac tissue characterization application 935. A screen 940 where the cardiac function application 931, the cardiac perfusion application 933, and the cardiac tissue characterization application 935 are executed is illustrated for convenience of explanation and may not be displayed on the output unit 120 (220) according to the embodiments.

Types of the first analysis value may include, for example, an analysis value of a ventricular wall thickness, an analysis value for ventricular wall thickening, and an analysis value for a ventricular wall motion. The MRI apparatus 100 (200) may generate bull's eye map images 901, 932, and 904 based on the first analysis value via the cardiac function application 931. Furthermore, the MRI apparatus 100 (200) may display at least one of the bull's eye map images 901, 932, and 904 respectively generated based on the analysis value for ventricular wall thickening, the analysis value of a ventricular wall thickness, and the analysis value for a ventricular wall motion, together with the first map image 903. According to the example shown in FIG. 9B, a user may select the analysis value of the ventricular wall thickness from among types of the first analysis value in order to generate the first map image 903.

Types of the second analysis value may include, for example, a time-to-peak value and an upslope value representing the degree of contrast enhancement when a contrast medium is injected into a muscle. The MRI apparatus 100 (200) may generate bull's eye map images 934 and 906 based on the second analysis value via the cardiac perfusion application 933. Furthermore, the MRI apparatus 100 (200) may display at least one of the bull's eye map images 934 and 906 respectively generated based on the upslope value and the time-to-peak value, together with the first map image 913. According to the example shown in FIG. 9B, the user may select the upslope value from among the types of the second analysis value in order to generate the first map image 913.

The third analysis value may be an analysis value for characteristics of a cardiac muscle tissue. The third analysis value may include an LGE volume representing a ratio of necrotic to normal tissue and the degree of necrosis and an analysis value obtained via an SIE category. The MRI apparatus 100 (200) may generate bull's eye map images 936 and 908 based on the third analysis value via the cardiac tissue characterization application 935. Furthermore, the MRI apparatus 100 (200) may display at least one of the bull's eye map images 936 and 908 respectively generated based on the LGE volume and the analysis value obtained via SIE category, together with the first map image 913. According to the example shown in FIG. 9B, the user may select the LGE volume from among the third analysis value in order to generate the first map image 913.

A color value of a subregion in the first map image 913 may be determined (designated) based on the first through third analysis values. For example, the MRI apparatus 100 (200) may determine (designate) a color value for the first map image 913 by combining first through third colors respectively represented on the bull's eye map images 932, 934, and 936. In detail, the MRI apparatus 100 (200) may determine a value of a color represented in subregion 1 of the first map image 913 by combining colors respectively represented in subregion 1 of the bull's eye map image 932, subregion 1 of the bull's eye map image 934, and subregion 1 of the bull's eye map image 936. Similarly, values of colors represented in subregions 2 through 17 of the first map image 903 may be determined in the same manner as described above.

Furthermore, the user may assign different weights to the first through third analysis values. For example, the user may apply weights of 0.1, 0.8, and 0.1 to the first through third analysis values, respectively. A method of combining the first through third colors respectively corresponding to the first through third analysis values will be described in more detail later with reference to FIGS. 10A through 10C.

According to the embodiment shown in FIG. 9B, if the user assesses the probability of heart disease based on a color indicated in a first map, it is possible to intuitively determine the probability of heart disease for each subregion of the heart.

Furthermore, the user may assess the probability of heart disease based on a combination of the first through third analysis values, instead of using the first through third analysis values individually. According to this combination method, the user may make a more accurate diagnosis than when assessing the probability of heart disease based on only one of the first through third analysis values.

Furthermore, the user may further improve accuracy of diagnosis by applying a larger weight to one of the first and second analysis values, on which the user desires to base the diagnosis.

FIG. 9C illustrates another example of a screen 950 on which a first map image 923 and a color map image 915 are displayed Referring now to FIG. 9C, the first map image 923 on the screen 950 may be a 3D image. The first map image 923 shown in FIG. 9C may be created based on at least two of a first analysis value obtained via a cardiac function application 931, a second analysis value obtained via a cardiac perfusion application 933, and a third analysis value obtained via a cardiac tissue characterization application 935.

The first map image 923 may include subregions (not shown) corresponding to subregions of the heart. Values of colors represented in the subregions of the first map image 923 may be determined in the same manner as described with reference to FIG. 9B. The determined values of colors may be indicated by respectively mapping the determined values of colors to the subregions of the heart. Since color values for the first map image 923 are determined in the same manner as described with reference to FIG. 9B, a detailed description thereof is omitted.

According to the embodiment shown in FIG. 9C, since positions of the subregions of the heart are indicated on the first map image 923, the user may more intuitively recognize the positions thereof when assessing the probability of heart disease based on colors represented in the first map image 923.

Figure 10C:
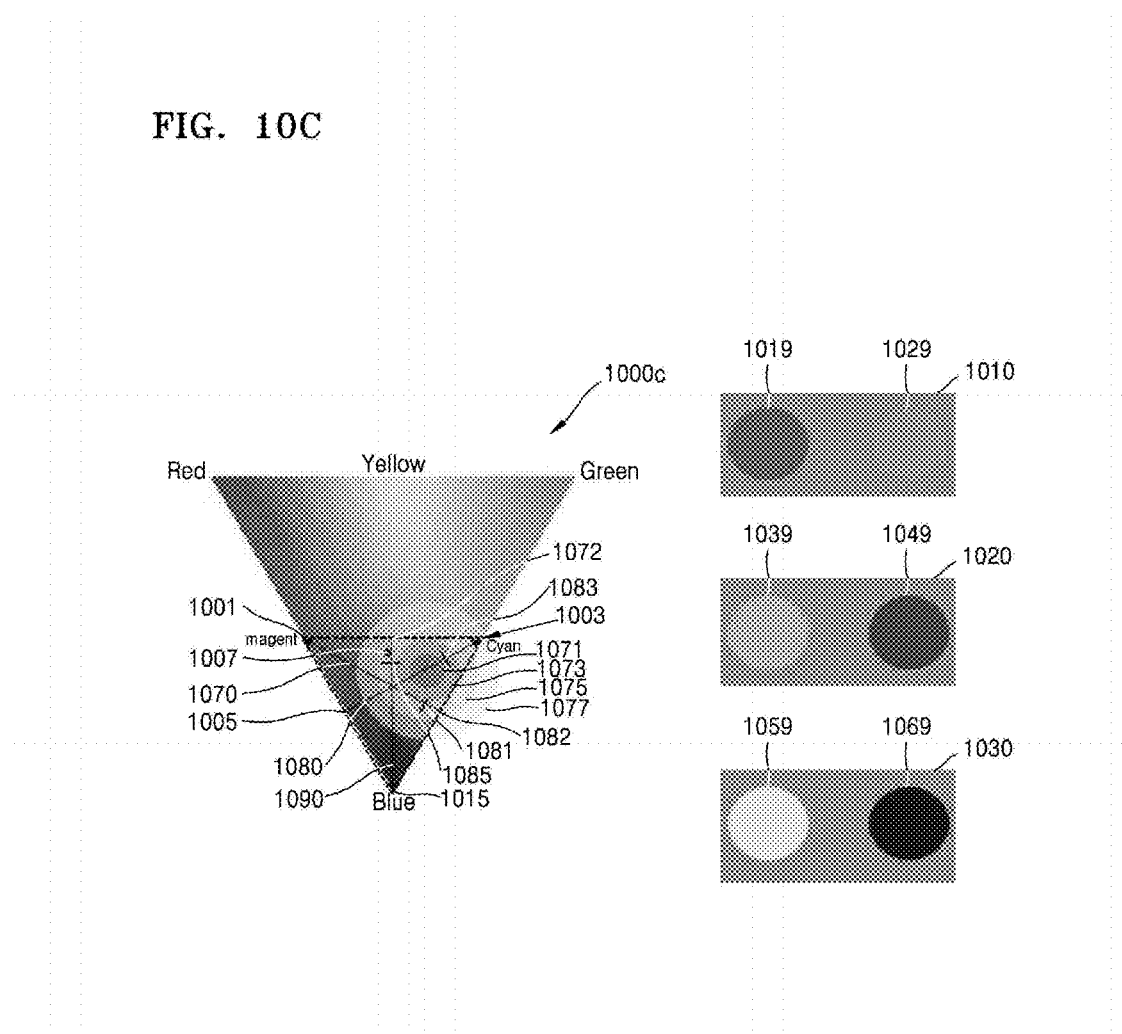

FIGS. 10A through 10C are color diagrams for explaining a method of determining a color value by combining at least two colors;

FIG. 10A is a diagram for explaining a method of determining a color value by combining at least two colors.

Referring now to FIG. 10A, color values from 0 to 100 are mapped onto a color bar 1002 that changes from a green color 1012 to a red color 1022. If a value of a color corresponding to a first analysis value is 20, a first color may correspond to a coordinate 1003. If a value of a color corresponding to a second analysis value is 30, a second color may correspond to a coordinate 1005.

According to the embodiment described with reference to FIG. 9A, if the first and second analysis values are combined, the first and second analysis values may be given the same weight of 0.5. In this case, when the first and second colors are combined, a combination of the first and second colors may be a color having a coordinate 1009 corresponding to a value of 25 (20×0.5+30×0.5) on the color bar 1002.

As another example, according to the embodiment described with reference to FIG. 9A, if the first and second analysis values are combined, weights of 0.1 and 0.9 may be respectively assigned to the first and second analysis values.

In this case, the first and second colors may be combined by respectively multiplying the value of 20 of the first color and the value of 30 of the second color by weights of 0.1 and 0.9. In other words, if weights of 0.1 and 0.9 are applied for combination of the first and second colors, a combination of the first and second colors may be a color having a coordinate 1007 corresponding to a value of 29 (20×0.1+30×0.9) on the color bar 1002.

FIG. 10B is a diagram for explaining a method of determining a color value by combining three colors.

FIG. 10B shows a color map 1000b for combining three colors when first through third analysis values are given the same weight. Referring to FIG. 10B, the first through third analysis values may correspond to coordinates on first through third color coordinate axes 1040, 1050, and 1060, respectively.

When the first analysis value ranges from 0 to 100, the first color coordinate axis 1040 may include coordinates 1001 and 1011 respectively corresponding to 0 and 100. The coordinates 1001 and 1011 may respectively correspond to a magenta color 1019 and a green color 1029, respectively. Colors corresponding to coordinates on the first color coordinate axis 1040 may change from the magenta color 1019 to the green color 1029 (1010).

When the second analysis value ranges from 0 to 100, the second color coordinate axis 1050 may include coordinates 1003 and 1013 respectively corresponding to 0 and 100. The coordinates 1003 and 1013 may respectively correspond to a cyan color 1039 and a red color 1049, respectively. Colors corresponding to coordinates on the second color coordinate axis 1050 may change from the cyan color 1039 to the red color 1049 (1020).

When the third analysis value ranges from 0 to 100, the third color coordinate axis 1060 may include coordinates 1005 and 1015 respectively corresponding to 0 and 100. The coordinates 1005 and 1015 may respectively correspond to a yellow color 1059 and a blue color 1069, respectively. Colors corresponding to coordinates on the third color coordinate axis 1060 may change from the yellow color 1059 to the blue color 1069 (1030).

For example, referring to FIG. 10B, a color value may be determined by at least two of the first through third analysis values respectively corresponding to the coordinates 1051, 1053, and 1055. According to an embodiment, the determined color value may be a value of the coordinates 1007 of a barycenter in a triangle formed by three points respectively having the coordinates 1051, 1053, and 1055.

A first circle 1031 depicted on the color map 1000b may be a region indicating that the probability of heart disease is 100%. A second circle 1033 may be a region indicating that the probability of heart disease is between 80% and 100%. A third circle 1035 may be a region indicating that the probability of heart disease is between 60% and 80%. A fourth circle 1037 may be a region indicating that the probability of heart disease is between 40% and 60%. The probability of heart disease may be assessed based on which region of the first through fourth circles 1031, 1033, 1035, and 1037 on the color map 1000b includes coordinates corresponding to a determined color value.

On the color map 1000b shown in FIG. 10B, the coordinates 1007 may be located at a boundary between the third and second circles 1035 and 1033 where the probability of heart disease is between 60% and 80% and between 80% and 100%, respectively. In this case, the user may determine that the probability of heart disease is about 80% based on the color map 1000b.

FIG. 10C is a color diagram for explaining a method of determining a color value by applying different weights when combining three colors.

FIG. 10C shows a color map 1000c for combining three colors when first through third analysis values are given different weights. For convenience of explanation, first through third color coordinate axes are not shown in FIG. 10C.

On the color map 1000c, positions of the first through fourth circles 1031, 1033, 1035, and 1037 depicted on the color map 1000b may be changed according to weights of the first through third analysis values. Circles 1071, 1073, 1075, and 1077 on the color map 1000c obtained by changing the positions of the first through fourth circles 1031, 1033, 1035, and 1037 respectively correspond to the first through fourth circles 1031, 1033, 1035, and 1037 on the color map 1000b.

A first weight coordinate axis 1070 representing a weight for the first analysis value includes coordinates 1082 when the weight is 0 and coordinates 1001 when the weight is 100. The second weight coordinate axis 1080 representing a weight for the second analysis value includes coordinates 1005 when the weight is 0 and coordinates 1003 when the weight is 100. The third weight coordinate axis 1090 representing a weight for the third analysis value includes, for example, coordinates 1072 when the weight is 0 and coordinates 1015 when the weight is 100.

For example, if weights for the first through third analysis values are 0.1, 0.8, and 0.1, respectively, a common center of the circles 1071, 1073, 1075, and 1077 may be a barycenter in a triangle formed by coordinates 1081, 1083, and 1085 respectively located on the first through third weight coordinate axes 1070, 1080, and 1090. In other words, if different weights are assigned to the first through third analysis values, the positions of the circles 1071, 1073, 1075, and 1077 may be shifted.

On the color map 1000c, coordinates 1007 may be located at a region corresponding to the circle 1075 where the probability of heart disease is between 80% and 100%. In this case, the user may determine that the probability of heart disease is between 80% and 100% based on the color map 1000c.

Figure 11:
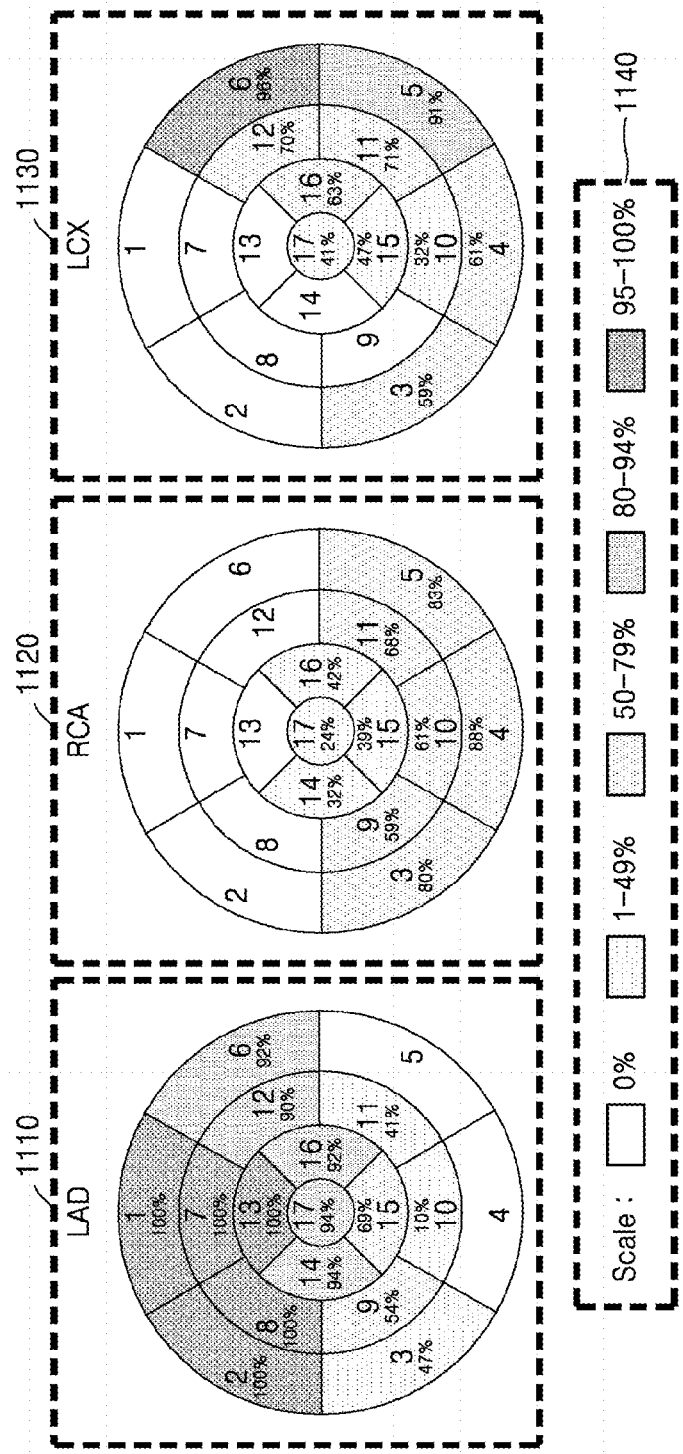
FIG. 11 is a diagram indicating which subregions in a bull's eye map correspond to a Left Anterior Descending Artery (LAD), a Left Circumflex Coronary Artery (LCX), and a Right Coronary Artery (RCA)

FIG. 11 is a diagram indicating what subregions in bull's eye maps 1110, 1120, and 1130 respectively correspond to a Left Anterior Descending Artery (LAD), a Right Coronary Artery (RCA), and a Left Circumflex Coronary Artery (LCX).

Figure 12:
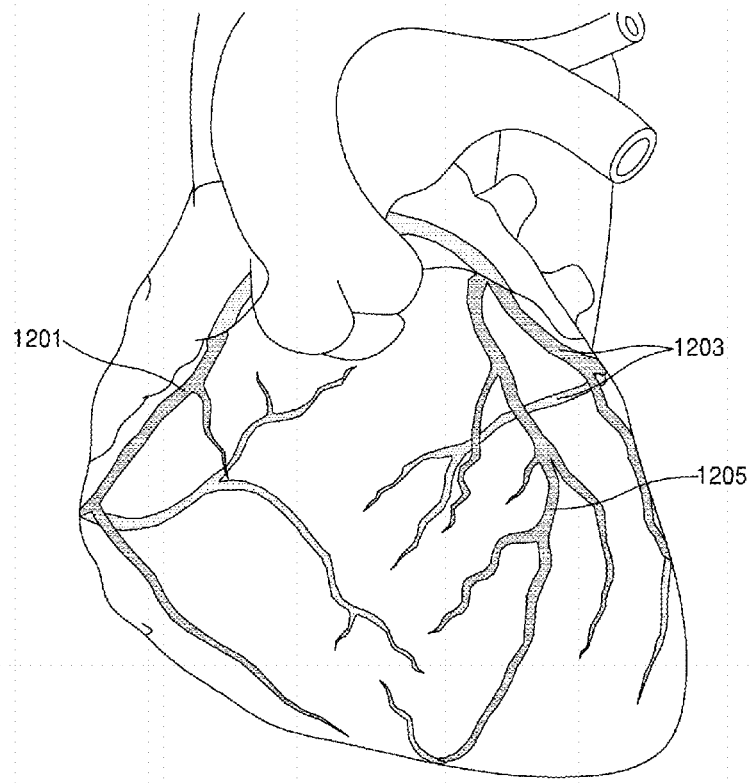
FIG. 12 illustrates positions of an LAD, an RCA, and an LCX included in a heart.

Coronary arteries included in the heart may include three blood vessels, i.e., an LAD, an LCX, and an RCA, and determining whether abnormality occurs in the three blood vessels is closely associated with diagnosis of heart disease. FIG. 12 shows positions 1205, 1201, and 1203 of the LAD, RCA, and LCX included in the heart.

The bull's eye map 1110 shows the probability that the LAD is present in subregions 1 through 17. The bull's eye map 1120 shows the probability that the RCA is present in subregions 1 through 17. The bull's eye map 1130 shows the probability that the LCA is present in subregions 1 through 17. Colors 1140 respectively corresponding to the probabilities of 0%, 1% to 49%, 50% to 70%, 80% to 94%, and 95% to 100% may be represented in each of the bull's eye maps 1110, 1120, and 1130.

The user may identify the positions of the LAD, LCX, and RCA based on the bull's eye maps 1110, 1120, and 1130. The user may also diagnose which of the LAD, LCX, and RCA has disease when assessing the probability of heart disease based on a first map image as described above with reference to FIGS. 9A through 9C.

Figure 13:
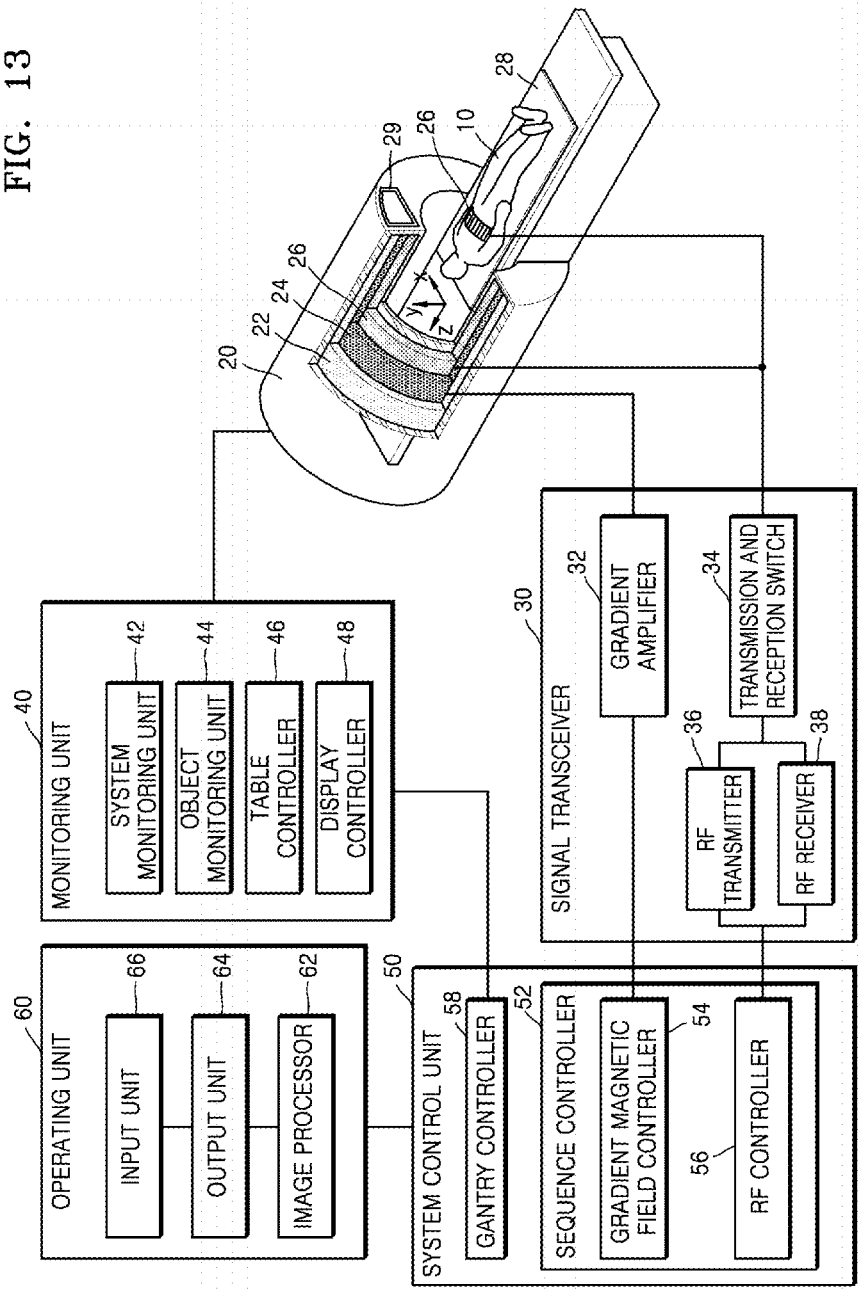
FIG. 13 is a schematic diagram of a general MRI system.

FIG. 13 is a block diagram of a general MRI system. Referring now to FIG. 13, the general MRI system may include a gantry 20, a signal transceiver 30, a monitoring unit 40, a system control unit 50, and an operating unit 60.

The gantry 20 prevents external emission of electromagnetic waves generated by a main magnet 22, a gradient coil 24, and an RF coil 26. A magnetostatic field and a gradient magnetic field are formed in a bore in the gantry 20, and an RF signal is emitted toward an object 10.

The main magnet 22, the gradient coil 24, and the RF coil 26 may be arranged in a predetermined direction of the gantry 20. The predetermined direction may be a coaxial cylinder direction. The object 10 may be disposed on a table 28 that is capable of being inserted into a cylinder along a horizontal axis of the cylinder.

The main magnet 22 generates a magnetostatic field or a static magnetic field for aligning magnetic dipole moments of atomic nuclei of the object 10 in a constant direction. A precise and accurate MR image of the object 10 may be obtained due to a magnetic field generated by the main magnet 22 being strong and uniform.

The gradient coil 24 includes X, Y, and Z coils for generating gradient magnetic fields in X-, Y-, and Z-axis directions crossing each other at right angles. The gradient coil 24 may provide location information of each region of the object 10 by differently inducing resonance frequencies according to the regions of the object 10.

The RF coil 26 may emit an RF signal toward a patient (object) and receive an MR signal emitted from the patient. In detail, the RF coil 26 may transmit, toward atomic nuclei included in the patient and having precessional motion, an RF signal having the same frequency as that of the precessional motion, stop transmitting the RF signal, and then receive an MR signal emitted from the atomic nuclei included in the patient.

For example, in order to transit an atomic nucleus from a low energy state to a high energy state, the RF coil 26 may generate and apply an electromagnetic wave signal that is an RF signal corresponding to a type of the atomic nucleus, to the object 10. When the electromagnetic wave signal generated by the RF coil 26 is applied to the atomic nucleus, the atomic nucleus may transit from the low energy state to the high energy state. Then, when electromagnetic waves generated by the RF coil 26 disappear, the atomic nucleus to which the electromagnetic waves were applied transits from the high energy state to the low energy state, thereby emitting electromagnetic waves having a Lamor frequency. In other words, when the applying of the electromagnetic wave signal to the atomic nucleus is stopped, an energy level of the atomic nucleus is changed from a high energy level to a low energy level, and thus the atomic nucleus may emit electromagnetic waves having a Lamor frequency. The RF coil 26 may receive electromagnetic wave signals from atomic nuclei included in the object 10.

The RF coil 26 may be realized as one RF transmitting and receiving coil having both a function of generating electromagnetic waves each having an RF that corresponds to a type of an atomic nucleus and a function of receiving electromagnetic waves emitted from an atomic nucleus. Alternatively, the RF coil 26 may be realized as a transmission RF coil having a function of generating electromagnetic waves each having an RF that corresponds to a type of an atomic nucleus, and a reception RF coil having a function of receiving electromagnetic waves emitted from an atomic nucleus.

The RF coil 26 may be fixed to the gantry 20 or may be detachable. When the RF coil 26 is detachable, the RF coil 26 may be an RF coil for a part of the object, such as a head RF coil, a chest RF coil, a leg RF coil, a neck RF coil, a shoulder RF coil, a wrist RF coil, or an ankle RF coil.

The RF coil 26 may communicate with an external apparatus via wires and/or wirelessly, and may also perform dual tune communication according to a communication frequency band.

The RF coil 26 may be a birdcage coil, a surface coil, or a transverse electromagnetic (TEM) coil according to structures.

The RF coil 26 may be a transmission exclusive coil, a reception exclusive coil, or a transmission and reception coil according to methods of transmitting and receiving an RF signal.

The RF coil 26 may be an RF coil having various numbers of channels, such as 16 channels, 32 channels, 72 channels, and 144 channels.

The gantry 20 may further include a display 29 disposed outside the gantry 20 and a display (not shown) disposed inside the gantry 20. The gantry 20 may provide predetermined information to the user or the object 10 through the display 29 and the display respectively disposed outside and inside the gantry 20.

The signal transceiver 30 may control the gradient magnetic field formed inside the gantry 20, i.e., in the bore, according to a predetermined MR sequence, and control transmission and reception of an RF signal and an MR signal.

The signal transceiver 30 may include, for example, a gradient amplifier 32, a transmission and reception switch 34, an RF transmitter 36, and an RF receiver 38.

The gradient amplifier 32 drives the gradient coil 24 included in the gantry 20, and may supply a pulse signal for generating a gradient magnetic field to the gradient coil 24 under the control of a gradient magnetic field controller 54. By controlling the pulse signal supplied from the gradient amplifier 32 to the gradient coil 24, gradient magnetic fields in X-, Y-, and Z-axis directions may be synthesized.

The RF transmitter 36 and the RF receiver 38 may drive the RF coil 26. The RF transmitter 36 may supply an RF pulse in a Lamor frequency to the RF coil 26, and the RF receiver 38 may receive an MR signal received by the RF coil 26.

The transmission and reception switch 34 may adjust transmitting and receiving directions of the RF signal and the MR signal. For example, the transmission and reception switch 34 may emit the RF signal toward the object 10 through the RF coil 26 during a transmission mode, and receive the MR signal from the object 10 through the RF coil 26 during a reception mode. The transmission and reception switch 34 may be controlled by a control signal output by an RF controller 56.

The monitoring unit 40 may monitor or control the gantry 20 or devices mounted on the gantry 20. The monitoring unit 40 may include a system monitoring unit 42, an object monitoring unit 44, a table controller 46, and a display controller 48.

The system monitoring unit 42 may monitor and control a state of the magnetostatic field, a state of the gradient magnetic field, a state of the RF signal, a state of the RF coil 26, a state of the table 28, a state of a device measuring body information of the object 10, a power supply state, a state of a thermal exchanger, and a state of a compressor.

The object monitoring unit 44 monitors a state of the object 10. In detail, the object monitoring unit 44 may include a camera for observing a movement or position of the object 10, a respiration measurer for measuring the respiration of the object 10, an electrocardiogram (ECG) measurer for measuring the electrical activity of the object 10, or a temperature measurer for measuring a temperature of the object 10.

The table controller 46 controls a movement of the table 28 where the object 10 is positioned. The table controller 46 may control the movement of the table 28 according to a sequence control of a sequence controller 50. For example, during moving imaging of the object 10, the table controller 46 may continuously or discontinuously move the table 28 according to the sequence control of the sequence controller 50, and thus the object 10 may be photographed in a field of view (FOV) larger than that of the gantry 20.

The display controller 48 controls the display 29 disposed outside the gantry 20 and the display disposed inside the gantry 20. In detail, the display controller 48 may control the display 29 and the display to be on or off, and may control a screen image to be output on the display 29 and the display. Also, when a speaker is located inside or outside the gantry 20, the display controller 48 may control the speaker to be on or off, or may control sound to be output via the speaker.

The system control unit 50 may include the sequence controller 52 for controlling a sequence of signals formed in the gantry 20, and a gantry controller 58 for controlling the gantry 20 and the devices mounted on the gantry 20.

The sequence controller 52 may include the gradient magnetic field controller 54 for controlling the gradient amplifier 32, and the RF controller 56 for controlling the RF transmitter 36, the RF receiver 38, and the transmission and reception switch 34. The sequence controller 52 may control the gradient amplifier 32, the RF transmitter 36, the RF receiver 38, and the transmission and reception switch 34 according to a pulse sequence received from the operating unit 60. Here, the pulse sequence includes all information required to control the gradient amplifier 32, the RF transmitter 36, the RF receiver 38, and the transmission and reception switch 34. For example, the pulse sequence may include information about a strength, an application time, and application timing of a pulse signal applied to the gradient coil 24.

The operating unit 60 may request the system control unit 50 to transmit pulse sequence information while controlling an overall operation of the MRI system.

The operating unit 60 may include an image processor 62 for receiving and processing the MR signal received by the RF receiver 38, an output unit 64, and an input unit 66.

The image processor 62 may process the MR signal received from the RF receiver 38 so as to generate MR image data of the object 10.

The image processor 62 receives the MR signal received by the RF receiver 38 and performs any one of various signal processes, such as amplification, frequency transformation, phase detection, low frequency amplification, and filtering, on the received MR signal.

The image processor 62 may arrange, for example, digital data in a k space (for example, also referred to as a Fourier space or a frequency space) of a memory, and rearrange the digital data into image data via 2D or 3D Fourier transformation.

If needed, the image processor 62 may perform a composition process or difference calculation process on the image data. The composition process may include an addition process on a pixel or a maximum intensity projection (MIP) process. The image processor 62 may store not only the rearranged image data but also image data on which a composition process or a difference calculation process is performed, in a memory or an external server.

The image processor 62 may perform any of the signal processes on the MR signal in parallel. For example, the image processor 62 may perform a signal process on a plurality of MR signals received by a multi-channel RF coil in parallel so as to rearrange the plurality of MR signals into image data.

The output unit 64 may output image data generated or rearranged by the image processor 62 to the user. The output unit 64 may also output information required for the user to manipulate the MRI system, such as a user interface (UI), user information, or object information. The output unit 64 may be a speaker, a printer, a cathode-ray tube (CRT) display, a liquid crystal display (LCD), a plasma display panel (PDP), an organic light-emitting device (OLED) display, a field emission display (FED), a light-emitting diode (LED) display, a vacuum fluorescent display (VFD), a digital light processing (DLP) display, a flat panel display (FPD), a 3-dimensional (3D) display, a transparent display, or any one of other various output devices that are well known to one of ordinary skill in the art.

The user may input object information, parameter information, a scan condition, a pulse sequence, or information about image composition or difference calculation by using the input unit 66. The input unit 66 may be a keyboard, a mouse, a track ball, a voice recognizer, a gesture recognizer, a touch screen, or any one of other various input devices that are well known to one of ordinary skill in the art.

The signal transceiver 30, the monitoring unit 40, the system control unit 50, and the operating unit 60 are shown as separate components in FIG. 8, but this arrangement is only for illustrative purposes, as respective functions of the signal transceiver 30, the monitoring unit 40, the system control unit 50, and the operating unit 60 may be performed by another component. For example, the image processor 62 converts the MR signal received from the RF receiver 38 into a digital signal in FIG. 1, but alternatively, the conversion of the MR signal into the digital signal may be performed by the RF receiver 38 or the RF coil 26.

The gantry 20, the RF coil 26, the signal transceiver 30, the monitoring unit 40, the system control unit 50, and the operating unit 60 may be connected to each other by wire or wirelessly, and when they are connected wirelessly, the MRI system may further include an apparatus (not shown) for synchronizing clock signals therebetween. Communication between the gantry 20, the RF coil 26, the signal transceiver 30, the monitoring unit 40, the system control unit 50, and the operating unit 60 may be performed by using a high-speed digital interface, such as low voltage differential signaling (LVDS), asynchronous serial communication, such as a universal asynchronous receiver transmitter (UART), a low-delay network protocol, such as error synchronous serial communication or a controller area network (CAN), or optical communication.

Figure 14:
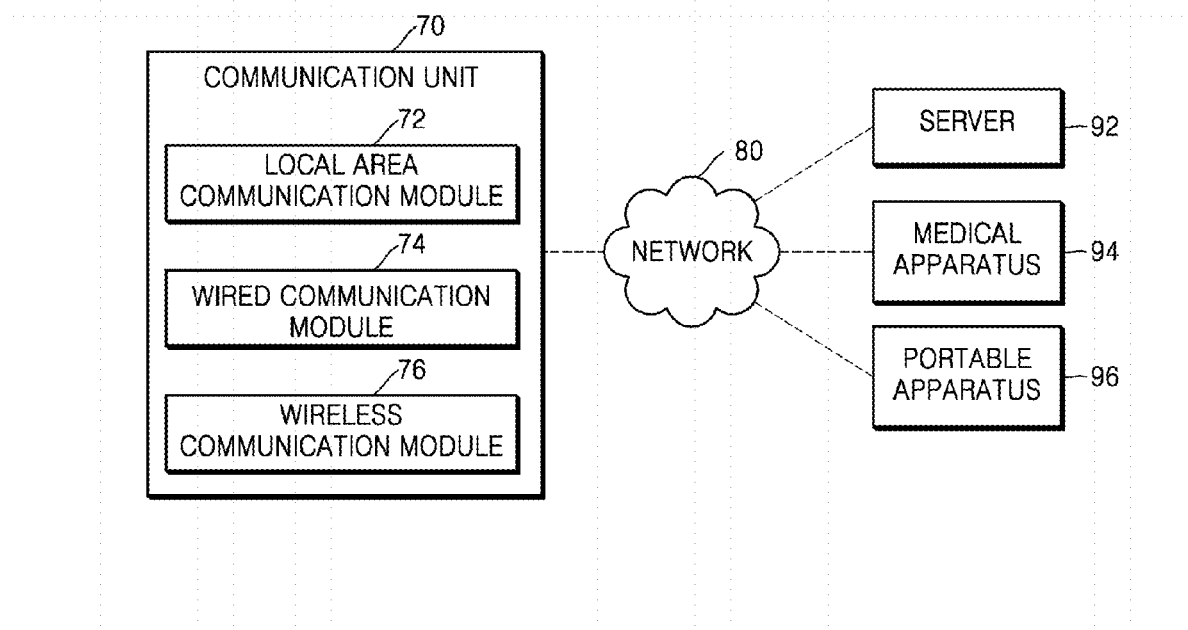
FIG. 14 is block diagram of a configuration of a communication unit.

FIG. 14 is a block diagram of a communication unit 70 according to an embodiment of the present disclosure.

Referring now to FIG. 14, the communication unit 70 may be connected to at least one selected from the gantry 20, the signal transceiver 30, the monitoring unit 40, the system control unit 50, and the operating unit 60 of FIG. 13.

The communication unit 70 may transmit and receive data to and from a hospital server or another medical apparatus in a hospital, which is connected through a picture archiving and communication system (PACS), and perform data communication according to the digital imaging and communications in medicine (DICOM) standard.

As shown in FIG. 14, the communication unit 70 may be connected to a network 80 by wire or wirelessly to communicate with a server 92, a medical apparatus 94, or a portable device 96.

In detail, the communication unit 70 may transmit and receive data related to the diagnosis of an object through the network 80, and may also transmit and receive a medical image captured by the medical apparatus 94, such as a CT apparatus, an MRI apparatus, or an X-ray apparatus. In addition, the communication unit 70 may receive a diagnosis history or a treatment schedule of the object from the server 92 and use the same to diagnose the object. The communication unit 70 may perform data communication not only with the server 92 or the medical apparatus 94 in a hospital, but also with the portable device 96, such as a mobile phone, a personal digital assistant (PDA), or a laptop of a doctor or patient.

Also, the communication unit 70 may transmit information about a malfunction of the MRI system or about a medical image quality to a user through the network 80, and receive a feedback regarding the information from the user.

The communication unit 70 may include at least one component enabling communication with an external apparatus.

For example, the communication unit 70 may include a local area communication module 72, a wired communication module 74, and a wireless communication module 76. The local area communication module 72 refers to a module for performing local area communication with an apparatus within a predetermined distance. Examples of local area communication technology according to an embodiment of the present include, but are not limited to, a wireless local area network (LAN), Wi-Fi, Bluetooth, ZigBee, Wi-Fi direct (WFD), ultra wideband (UWB), infrared data association (IrDA), Bluetooth low energy (BLE), and near field communication (NFC).

The wired communication module 74 refers to a module for performing communication by using an electric signal or an optical signal. Examples of wired communication technology according to an embodiment of the present disclosure include wired communication techniques using a pair cable, a coaxial cable, and an optical fiber cable, and other well-known wired communication techniques.

The wireless communication module 76 transmits and receives a wireless signal to and from at least one selected from a base station, an external apparatus, and a server in a mobile communication network. Here, the wireless signal may be, for example, a voice call signal, a video call signal, or data in any one of various formats according to transmission and reception of a text/multimedia message.

The MRI apparatus 100 (200) of FIG. 1 (2) may be the external server 92, medical apparatus 94, or portable device 96 connected to an MRI system. In other words, the MRI apparatus 100 (200) may be connected to the communication unit 70 shown in FIG. 14 to be operated.

The apparatuses and methods of the disclosure can be implemented in hardware, and in part as firmware or via the execution of software or computer code in conjunction with hardware that is stored on a non-transitory machine readable medium such as a CD ROM, a RAM, a floppy disk, a hard disk, or a magneto-optical disk, or computer code downloaded over a network originally stored on a remote recording medium or a non-transitory machine readable medium and stored on a local non-transitory recording medium for execution by hardware such as a processor, so that the methods described herein are loaded into hardware such as a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc., that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein. In addition, an artisan understands and appreciates that a "processor", "microprocessor" "controller", or "control unit" constitute hardware in the claimed disclosure that contain circuitry that is configured for operation. Under the broadest reasonable interpretation, the appended claims constitute statutory subject matter in compliance with 35 U.S.C. §101 and none of the elements are software per se.

The definition of the terms "unit" or "module" as referred to herein are to be understood as constituting hardware circuitry such as a CCD, CMOS, SoC, AISC, FPGA, a processor or microprocessor (a controller) configured for a certain desired functionality, or a communication module containing hardware such as transmitter, receiver or transceiver, or a non-transitory medium comprising machine executable code that is loaded into and executed by hardware for operation, in accordance with statutory subject matter under 35 U.S.C. §101 and do not constitute software per se. For example, the image processor in the present disclosure, and any references to an input unit and/or an output unit both comprise hardware circuitry configured for operation.

Examples of the computer-readable non-transitory recording medium include magnetic storage media (e.g., ROM, floppy disks, hard disks, etc.), optical recording media (e.g., CD-ROMs or DVDs), etc.

While the present disclosure has been particularly shown and described with reference to embodiments thereof, it will be understood by those of ordinary skill in the art that various changes in form and details may be made therein without departing from the spirit and scope of the present disclosure as defined by the following claims. Accordingly, the above embodiments and all aspects thereof are examples only and are not limiting.

What is claimed is:

1. A medical imaging apparatus comprising:
    a magnetic resonance imaging (MRI) system configured to transmit radio frequency (RF) signals towards an organ with one or more RF coils and receive RF signals from the organ with the one or more RF coils;
    an image processor configured to process an image of the organ based on the received RF signals by obtaining a first bull's eye map indicating colors corresponding to one analysis value among a plurality of analysis values for each subregions of the organ, obtaining a second bull's eye map indicating colors corresponding to another analysts value among the plurality of analysis values for each of the subregions of the organ, designating respective color values for the subregions of the image of the organ by combining colors of the first bull's eye map and colors of the second bull's eye map, and obtaining a first map image by repetitively mapping the combined colors to corresponding subregions and indicating the combined colors on the subregions; and a display configured to display the first map image.

2. The medical imaging apparatus of claim 1, wherein the image of the organ comprises an image of a heart, and the subregions comprises respective parts of the heart.

3. The medical imaging apparatus of claim 2,
wherein the plurality of analysis values comprise a first analysis value, a second analysis value, and a third analysis value,
wherein the first analysis value is determined based on a function of a muscle for each of the subregions of a heart,
wherein the second analysis value is determined based on perfusion of a heart muscle for each of the subregions, and
wherein the third analysis value is determined based on characteristics of a tissue of the heart muscle for each of the subregions.

4. The medical imaging apparatus of claim 2, wherein the display further outputs a displays of at least one of a color bar image and a color map image that show probabilities of heart disease corresponding to a plurality of combined colors.

5. The medical imaging apparatus of claim 1,
wherein the plurality of analysis values comprise a first analysis value, a second analysis value, and a third analysis value,
further comprising an input unit configured to receive a selection of at least one of the first through third analysis values.

6. The medical imaging apparatus of claim 1,
wherein the plurality of analysis values comprise a first analysis value, a second analysis value, and a third analysis value,
wherein the image processor is configured to map the first analysis value, the second analysis value, and the third analysis value according to a first color, a second color and a third color, respectively, and
wherein the combined colors are designated by combining at least two of the first color, second color and third color.

7. The medical imaging apparatus of claim 6, wherein the image processor determines the combined colors by combining at least two of the first color, second color, and third color based on a weight for at least one of the first analysis value, second analysis value and third analysis value.

8. The medical imaging apparatus of claim 6, wherein the display outputs a display of at least one of a first additional image, a second additional image, and a third additional image, respectively, indicating the first color, the second color and the third color.

9. The medical imaging apparatus of claim 1, wherein the display displays an output of a graph related to at least one of the plurality of analysis values.

10. The medical imaging apparatus of claim 1, wherein the first map image comprises at least one of a two-dimensional (2D) bull's eye map and a three-dimensional (3D) bull's eye map.

11. The medical imaging apparatus of claim 1, wherein the image processor is configured in response to user selection to apply a weight to an analysis value on which a diagnosis is based, and to apply a larger weight to one of the analysis values from among a plurality of analysis values.

12. A medical imaging system comprising:
the medical imaging apparatus of claim 1; and
a signal transceiver configured to send and receive a medical image.

13. A method of processing a medical image, the method comprising:
transmitting radio frequency (RF) signals towards an organ with one or more RF coils;
receiving RF signals from the organ with the one or more RF coils,
obtaining a first bull's eye map indicating color corresponding to one analysis value among a plurality of analysis values for each of subregions of the organ;
obtaining a second bull's eye map indicating colors corresponding to another analysis value among a plurality of analysis values tot each of the subregions of the organ;
designating by an image processor respective color values for the subregions of an image of the organ by combining colors of the first bull's eye map and colors of the second bull's eye map; and
obtaining a first map image by repetitively mapping the combined colors to corresponding subregions and indicating the combined colors on the subregions; and
displaying a first map image.

14. The method according to claim 13, wherein the image of the organ comprises an image of a heart, and the subregions comprise respective parts of the heart.

15. The method of claim 14,
wherein the plurality of analysis values comprise a first analysis value, a second analysis value, and a third analysis value,
wherein the first analysis value of the subregions is determined based on a function of a muscle of the heart for each of the subregions,
wherein the second analysis value is determined based on perfusion of the heart muscle for each of the subregions, and
wherein the third analysis value is determined based on characteristics of a tissue of the heart muscle for each of the subregions.

16. The method of claim 14,
wherein the plurality of analysis values comprise a first analysis value, a second analysis value, and a third analysis value, the method further comprising receiving a user input r selecting at least one of the first analysis value, second analysis value, and third analysis value.

17. The method of claim 14,
wherein the plurality of analysis values comprise a first analysis value, a second analysis value, and a third analysis value;
wherein the designating of the combined colors for the subregions of the heart comprises:
mapping the first through third analysis values to first through third colors, respectively; and
designating the color values by combining at least two of the first through third colors.

18. The method of claim 17, wherein the designating of the combined colors by combining the at least two of the first through third colors comprises combining based on a weight for at least one of the first through third analysis values.

19. The method of claim 17, wherein the displaying of the first map image further comprises displaying at least one additional image out of a first through third additional images respectively indicating the first through third colors.

20. The method of claim 14, wherein the displaying of the first map image further comprises displaying at least one of a color bar image and a color map image that show probabilities of heart disease that corresponds to a plurality of combined colors.

21. The method of claim 14, wherein the first map image comprises at least lone of a two-dimensional (2D) bull's eye map and a three-dimensional (3D) bull's eye map.

22. The method of claim 14, further comprising applying by the image processor in response to user selection a weight to an analysis value on which a diagnosis is based, and to apply a larger weight to one of the analysis values from among a plurality of analysis values.

23. The method of claim 13, wherein the displaying of the first map image includes displaying a screen that shows a third image and a graphical display related to at least one of the plurality of analysis values.

24. A non-transitory computer-readable recording medium having recorded thereon a program for executing the method of claim 13.

\* \* \* \* \*